United States Patent
Braganca et al.

(10) Patent No.: US 12,306,179 B2
(45) Date of Patent: May 20, 2025

(54) THERMAL SENSOR ARRAY FOR MOLECULE DETECTION AND RELATED DETECTION SCHEMES

(71) Applicant: Western Digital Technologies, Inc., San Jose, CA (US)

(72) Inventors: Patrick Braganca, San Jose, CA (US); Daniel Bedau, San Jose, CA (US)

(73) Assignee: Western Digital Technologies, Inc., San Jose, CA (US)

( * ) Notice: Subject to any disclaimer, the term of this patent is extended or adjusted under 35 U.S.C. 154(b) by 666 days.

(21) Appl. No.: 17/661,578

(22) Filed: May 2, 2022

(65) Prior Publication Data

US 2022/0252587 A1    Aug. 11, 2022

Related U.S. Application Data

(62) Division of application No. 16/697,013, filed on Nov. 26, 2019, now Pat. No. 11,327,073.

(60) Provisional application No. 62/833,222, filed on Apr. 12, 2019.

(51) Int. Cl.
  G01N 33/543    (2006.01)
  C12Q 1/6869    (2018.01)
  G01K 13/02    (2021.01)

(52) U.S. Cl.
  CPC ..... *G01N 33/54346* (2013.01); *C12Q 1/6869* (2013.01); *G01K 13/02* (2013.01); *G01N 33/54326* (2013.01); *C12Q 2563/107* (2013.01)

(58) Field of Classification Search
  CPC ....... G01N 33/54346; G01N 33/54326; G01N 27/745; G01N 33/54373; G01N 33/54333; C12Q 1/6869; C12Q 2563/107; C12Q 2563/143; C12Q 2563/149; C12Q 2565/607; C12Q 2565/625; G01K 13/02; G01K 1/026
See application file for complete search history.

(56) References Cited

U.S. PATENT DOCUMENTS

| | | |
|---|---|---|
| 5,200,084 A | 4/1993 | Liberti et al. |
| 5,302,509 A | 4/1994 | Cheeseman |
| 6,037,167 A | 3/2000 | Adelman et al. |
| 6,046,585 A | 4/2000 | Simmonds |
| 6,197,520 B1 | 3/2001 | Wittwer et al. |
| 6,406,848 B1 | 6/2002 | Bridgham et al. |
| 6,654,505 B2 | 11/2003 | Bridgham et al. |
| 6,806,052 B2 | 10/2004 | Bridgham et al. |
| 6,831,994 B2 | 12/2004 | Bridgham et al. |
| 6,833,246 B2 | 12/2004 | Balasubramanian |
| 6,905,736 B1 | 6/2005 | Chow et al. |
| 6,969,488 B2 | 11/2005 | Bridgham et al. |
| 6,969,679 B2 | 11/2005 | Okamura et al. |
| 7,057,026 B2 | 6/2006 | Barnes et al. |
| 7,115,400 B1 | 10/2006 | Adessi et al. |
| 7,282,370 B2 | 10/2007 | Bridgham et al. |
| 7,382,586 B2 | 6/2008 | Carey et al. |
| 7,405,281 B2 | 7/2008 | Xu et al. |
| 7,414,116 B2 | 8/2008 | Milton et al. |
| 7,427,673 B2 | 9/2008 | Balasubramanian et al. |
| 7,473,031 B2 | 1/2009 | Wolkin et al. |
| 7,541,444 B2 | 6/2009 | Milton et al. |
| 7,566,537 B2 | 7/2009 | Balasubramanian et al. |
| 7,771,973 B2 | 8/2010 | Milton et al. |
| 7,772,384 B2 | 8/2010 | Balasubramanian et al. |
| 7,920,032 B2 | 4/2011 | Makinwa et al. |
| 8,053,244 B2 | 11/2011 | Ryan et al. |
| 8,058,031 B2 | 11/2011 | Xu et al. |
| 8,071,739 B2 | 12/2011 | Milton et al. |
| 8,130,072 B2 | 3/2012 | De Bruyker et al. |
| 8,158,346 B2 | 4/2012 | Balasubramanian et al. |
| 8,252,910 B2 | 8/2012 | Korlach et al. |
| 8,259,409 B2 | 9/2012 | Braganca et al. |
| 8,361,713 B2 | 1/2013 | Bridgham et al. |
| 8,367,813 B2 | 2/2013 | Korlach |

(Continued)

FOREIGN PATENT DOCUMENTS

| CN | 1947016 A | 4/2007 |
|---|---|---|
| CN | 201016817 Y | 2/2008 |

(Continued)

OTHER PUBLICATIONS

A. Seki, et al., "Study of the heating characteristics and mechanisms of magnetic nanoparticles over a wide range of frequencies and amplitudes of an alternating magnetic field," Journal of Physics: Conference Series 521 (2014).

A.M. Sydor et al., "Super-Resolution Microscopy: From Single Molecules to Supramolecular Assemblies," Trends in Cell Biology, Dec. 2015, vol. 25, No. 12, pp. 730-748.

B. N. Engel, et al., "A 4-Mb Toggle MRAM Based on a Novel Bit and Switching Method," IEEE Transactions on Magnetics, vol. 41, No. 1, Jan. 2005.

C. Chappert et al., "The emergence of spin electronics in data storage," Nature Materials, Dec. 2007.

C.H. Smith et al., "High-resolution giant magnetoresistance on-chip arrays for magnetic imaging," Journal of Applied Physics 93, 6864 (2003).

(Continued)

*Primary Examiner* — Narayan K Bhat

(57) ABSTRACT

Disclosed herein are methods of using detection devices. A detection device comprises a fluidic channel configured to receive a plurality of molecules to be detected, a plurality of temperature sensors, and an insulating material encapsulating the plurality of temperature sensors and providing a barrier between the plurality of temperature sensors and contents of the fluidic channel. A surface of the insulating material within the fluidic channel provides a plurality of sites for binding the plurality of molecules to be detected. Each of the plurality of temperature sensors is configured to detect, in the presence of an alternating magnetic field, a temperature change indicating presence or absence of one or more magnetic nanoparticles (MNPs) coupled to at least one of the plurality of molecules to be detected at a respective subset of the plurality of sites.

24 Claims, 17 Drawing Sheets

(56) References Cited

U.S. PATENT DOCUMENTS

| | | | |
|---|---|---|---|
| 8,432,644 | B2 | 4/2013 | Braganca et al. |
| 8,462,461 | B2 | 6/2013 | Braganca et al. |
| 8,513,029 | B2 | 8/2013 | Zhou |
| 8,553,346 | B2 | 10/2013 | Braganca et al. |
| 8,570,677 | B2 | 10/2013 | Braganca et al. |
| 8,597,881 | B2 | 12/2013 | Milton et al. |
| 8,652,810 | B2 | 2/2014 | Adessi et al. |
| 8,654,465 | B2 | 2/2014 | Braganca et al. |
| 8,675,309 | B2 | 3/2014 | Braganca et al. |
| 8,728,729 | B2 | 5/2014 | Bridgham et al. |
| 8,728,825 | B2 | 5/2014 | Wang et al. |
| 9,121,062 | B2 | 9/2015 | Balasubramanian et al. |
| 9,273,354 | B2 | 3/2016 | Bridgham et al. |
| 9,297,006 | B2 | 3/2016 | Adessi et al. |
| 9,435,791 | B2 | 9/2016 | Acosta et al. |
| 9,453,258 | B2 | 9/2016 | Kain et al. |
| 9,464,107 | B2 | 10/2016 | Wegener et al. |
| 9,587,275 | B2 | 3/2017 | Emig et al. |
| 9,605,310 | B2 | 3/2017 | Balasubramanian et al. |
| 9,640,748 | B2 | 5/2017 | Gotsmann et al. |
| 10,203,379 | B2 | 2/2019 | Wang et al. |
| 10,260,095 | B2 | 4/2019 | Esfandyarpour et al. |
| 10,591,440 | B2 | 3/2020 | Astier et al. |
| 2004/0043479 | A1* | 3/2004 | Briscoe ............. G01N 30/6095 435/288.5 |
| 2004/0219695 | A1 | 11/2004 | Fox |
| 2005/0054081 | A1 | 3/2005 | Hassard et al. |
| 2005/0087000 | A1 | 4/2005 | Coehoorn et al. |
| 2005/0100930 | A1 | 5/2005 | Wang et al. |
| 2005/0118102 | A1 | 6/2005 | Xiang et al. |
| 2006/0226832 | A1 | 10/2006 | Ikeda et al. |
| 2007/0224700 | A1 | 9/2007 | Masters |
| 2007/0264159 | A1 | 11/2007 | Graham et al. |
| 2008/0218165 | A1 | 9/2008 | Kahlman et al. |
| 2008/0241569 | A1 | 10/2008 | Qin et al. |
| 2009/0148857 | A1 | 6/2009 | Srivastava et al. |
| 2009/0206832 | A1 | 8/2009 | Kahlman et al. |
| 2009/0208957 | A1 | 8/2009 | Korlach et al. |
| 2010/0039105 | A1 | 2/2010 | Ryan et al. |
| 2010/0111768 | A1 | 5/2010 | Banerjee et al. |
| 2010/0194386 | A1 | 8/2010 | Prins et al. |
| 2010/0207631 | A1 | 8/2010 | McDowell |
| 2010/0231214 | A1 | 9/2010 | Zhou |
| 2010/0248973 | A1 | 9/2010 | Lankvelt et al. |
| 2010/0291558 | A1 | 11/2010 | Kim |
| 2011/0223612 | A1 | 9/2011 | Wang et al. |
| 2012/0214171 | A1 | 8/2012 | Kotseroglou |
| 2012/0295262 | A1 | 11/2012 | Ronaghi et al. |
| 2014/0008281 | A1 | 1/2014 | Ramanathan et al. |
| 2014/0099663 | A1 | 4/2014 | Wang et al. |
| 2014/0139214 | A1 | 5/2014 | Park et al. |
| 2014/0292318 | A1 | 10/2014 | Wang et al. |
| 2016/0131613 | A1 | 5/2016 | Jayant et al. |
| 2016/0139035 | A1 | 5/2016 | Florescu et al. |
| 2017/0097337 | A1 | 4/2017 | Shultz et al. |
| 2017/0304825 | A1 | 10/2017 | Issadore et al. |
| 2018/0074016 | A1 | 3/2018 | Chen et al. |
| 2018/0100190 | A1 | 4/2018 | Esfandyarpour et al. |
| 2018/0128822 | A1 | 5/2018 | Wang et al. |
| 2018/0237850 | A1 | 8/2018 | Mandell et al. |
| 2018/0284200 | A1 | 10/2018 | Chen et al. |
| 2019/0032114 | A1* | 1/2019 | Trivedi ................ B01L 3/5027 |
| 2019/0170680 | A1 | 6/2019 | Sikora et al. |
| 2019/0390267 | A1 | 12/2019 | Astier et al. |
| 2021/0047681 | A1 | 2/2021 | Mendonsa et al. |
| 2021/0047682 | A1 | 2/2021 | Mendonsa et al. |

FOREIGN PATENT DOCUMENTS

| | | |
|---|---|---|
| CN | 102928596 A | 2/2013 |
| CN | 103885000 A | 6/2014 |
| CN | 105112516 A | 12/2015 |
| CN | 106153207 A | 11/2016 |
| CN | 107873060 A | 4/2018 |
| CN | 107923910 A | 4/2018 |
| CN | 108138229 A | 6/2018 |
| CN | 107051597 B | 8/2019 |
| EP | 1544310 A2 | 6/2005 |
| EP | 2674264 A2 | 12/2013 |
| EP | 3208627 A1 | 8/2017 |
| ES | 2674264 | 6/2018 |
| JP | 2005315677 A | 11/2005 |
| WO | 2005047864 A3 | 9/2005 |
| WO | 2005124345 A2 | 12/2005 |
| WO | 2009001280 A2 | 12/2008 |
| WO | 2015031691 A1 | 3/2015 |
| WO | 2016183218 A1 | 11/2016 |
| WO | 2017030999 A1 | 2/2017 |
| WO | 2017061129 A1 | 4/2017 |
| WO | 2018017884 A1 | 1/2018 |
| WO | 2018186539 A1 | 10/2018 |
| WO | 2018226876 A1 | 12/2018 |
| WO | 2019060628 A1 | 3/2019 |
| WO | 2019068204 A1 | 4/2019 |
| WO | 2020210370 A1 | 10/2020 |

OTHER PUBLICATIONS

D. Ross et al., "Temperature Measurement in Microfluidic Systems Using a Temperature-Dependent Fluorescent Dye," Anal. Chem. 2001, 73, 17, 4117-4123, Jul. 24, 2001.

Daschiel et al. The holy grail of microfluidics: sub-laminar drag by layout of periodically embedded microgrooves (2013) MicrofluidNanofluid 15, 675-687.

E. du Trémolet de Lacheisserie, D. Gignoux, and M. Schlenker (editors), Magnetism: Materials and Applications, vol. 2. Springer, 2005.

E. Hall, "On a New Action of the Magnet on Electric Currents," American Journal of Mathematics, vol. 2, 287, 1879.

ePHOTOzine.com, "Complete Guide To Image Sensor Pixel Size," Aug. 2, 2016, available at https://www.ephotozine.com/article/complete-guide-to-image-sensor-pixel-size-29652.

F. Grasset et al., "Synthesis, magnetic properties, surface modification and cytotoxicity evaluation of Y3Fe5-xAlxO12 (0?x?2) garnet submicron particles for biomedical applications," Journal of Magnetism and Magnetic Materials, vol. 234, Issue 3, Sep. 2001, pp. 409-418.

F. Menges et al., "Temperature mapping of operating nanoscale devices by scanning probe thermometry," Nature Communications, 7:10874, Mar. 3, 2016.

G. Li, S. Sun, R. J. Wilson, R. L. White, N. Pourmand, S. X. Wang, "Spin valve sensors for ultrasensitive detection of superparamagnetic nanoparticles for biological applications," Sensors and Actuators, vol. 126, 98, 2006.

Illumina, "Illumina CMOS Chip and One-Channel SBS Chemistry," document No. 770-2013-054-B, 2018 (available at https://www.illumina.com/content/dam/illumina-marketing/documents/products/techspotlights/cmos-tech-note-770-2013-054.pdf).

Illumina, "NovaSeq 6000 Sequencing System," 2019, available at https://www.illumina.com/systems/sequencing-platforms/novaseq.html.

International Search Report and Written Opinion from PCT Application No. PCT/US2019/068131 (filed Dec. 20, 2019), mailed Apr. 1, 2020.

International Search Report and Written Opinion from PCT Application No. PCT/US2019/068535 (filed Dec. 26, 2019), mailed Apr. 26, 2020.

International Search Report and Written Opinion from PCT Application No. PCT/US2020/014707 (filed Jan. 23, 2020), mailed May 11, 2020.

International Search Report and Written Opinion from PCT Application No. PCT/US2020/021776 (filed Mar. 9, 2020), mailed Sep. 1, 2020.

International Search Report and Written Opinion from PCT Application No. PCT/US2020/023069 (filed Mar. 17, 2020), mailed Jul. 20, 2020.

(56) References Cited

OTHER PUBLICATIONS

International Search Report and Written Opinion from PCT Application No. PCT/US2020/023078 (filed Mar. 17, 2020), mailed Jul. 19, 2020.
International Search Report and Written Opinion from PCT Application No. PCT/US2020/027290 (filed Apr. 8, 2020), mailed Jun. 25, 2020.
International Search Report and Written Opinion from PCT Application No. PCT/US2020/035915 (filed Jun. 3, 2020), mailed Aug. 26, 2020.
International Search Report and Written Opinion from PCT Application No. PCT/US2021/021274 (filed Mar. 7, 2021), mailed Sep. 28, 2021.
International Search Report and Written Opinion from PCT Application No. PCT/US2021/028263 (filed Apr. 21, 2021), mailed Aug. 26, 2021.
International Search Report and Written Opinion from PCT Application No. PCT/US2021/040767 (filed Jul. 8, 2021), mailed Oct. 25, 2021.
International Search Report from PCT App. No. PCT/US2016/046888, mailed Oct. 26, 2016.
J. C. Slonczewski, "Current-driven excitation of magnetic multilayers," Journal of Magnetism and Magnetic Materials, vol. 159, L1, 1996.
J. Sakakibara et al., "Measurements of thermally stratified pipe flow using image-processing techniques," Experiments in Fluids, Dec. 1993, vol. 16, Issue 2, pp. 82-96.
John Pearce, et al., "Magnetic Heating of Nanoparticles: The Importance of Particle Clustering to Achieve Therapeutic Temperatures," Journal of Nanotechnology in Engineering and Medicine, Feb. 2014, vol. 4 / 011007-1.
L. Berger, "Emission of spin waves by a magnetic multilayer traversed by a current," Physical Review B, vol. 54, 9353, 1996.
Lany, M., G. Boero, and R. S. Popovic. "Superparamagnetic microbead inductive detector". Review of scientific instruments 76.8 (2005): 084301.
Latha, G., Kumar, P. D., Gopi, K., Srikanth, P., Kusumalatha, Y., & Babu, G. V. (2017). A review on magnetic micro/nanoparticles. World J. Pharm. Res, 6, 341-366.
Lin Gui and Carolyn L. Ren, "Temperature measurement in microfluidic chips using photobleaching of a fluorescent thin film," Applied Physics Letters 92, 024102, 2008.
M. Aslam et al., "Silica encapsulation and magnetic properties of FePt nanoparticles," Journal of Colloid and Interface Science 290 (2005) 444-449.
M. Díaz-Michelena, "Small Magnetic Sensors for Space Applications," Sensors, vol. 9, 2271, 2009.
M. Hisham Alnasir et al., "Magnetic and magnetothermal studies of pure and doped gadolinium silicide nanoparticles for self-controlled hyperthermia applications," Journal of Magnetism and Magnetic Materials, vol. 449, Mar. 1, 2018, pp. 137-144.
M.T. Tlili et al., "Magnetic, Electrical Properties and Spin-Glass Effect of Substitution of Ca for Pr in Ca2—xPrxMn04 Compounds," The Open Surface Science Journal, 2009, vol. 1, pp. 54-58.
Mao et al. A Microfluidic Device with a Linear Temperature Gradient for Parallel and Combinatorial Measurements (2002) J AmChem Soc 124, 4432-4435.
Michael L. Metzker, "Sequencing Technologies—the Next Generation," Nature Rev. Genet. 11: 31-46 (2009).
Miller, M. M., et al. "A Dna array sensor utilizing magnetic microbeads and magnetoelectronic detection". Journal of Magnetism and Magnetic Materials 225.1-2 (2001): 138-144.
N. X. Phuc, et al., "Tuning of the Curie Temperature in La1—xSrxMn1—yTiyO3" J. Korean Phy. Soc., vol. 52, No. 5, May 2008, pp. 1492-1495.
N.R. Patil et al., "Effect of temperature on the fluorescence emission of ENCTTTC in different nonpolar solvents," Can. J. Phys. 91: 971-975 (2013).

P. Anderson, J. Rowell, "Probable Observation of the Josephson Superconducting Tunneling Effect," Physical Review Letters, vol. 10, 230, 1963.
P. M. Braganca, B. A. Gurney, B. A. Wilson, J. A. Katine, S. Maat and J. R. Childress, "Nanoscale magnetic field detection using a spin torque oscillator," Nanotechnology, vol. 21, 235202, 2010.
P. Namdari, H. Daraee, and A. Eatemadi, "Recent Advances in Silicon Nanowire Biosensors: Synthesis Methods, Properties and Applications", Nanoscale Research Letters, vol. 11, 406, 2016.
Qiu et al. Instrument-free point-of-care molecular diagnosis of H 1 N 1 based on microfluidic convective PCR (2017) Sensors andActuators B: Chemical 243, 738-744.
Quynh, L. K., et al. Detection of magnetic nanoparticles using simple AMR sensors in Wheatstone bridge. Journal of Science: Advanced Materials and Devices, 2016, 1.1: 98-102.
R. C. Jaklevic, J. Lambe, A. H. Silver & J. E. Mercereau, "Quantum Interference Effects in Josephson Tunneling," Physical Review Letters, vol. 12, 159, 1964.
R. Giri, "Temperature effect study upon the fluorescence emission of substituted coumarins," Spectrochimica Acta Part A: Molecular Spectroscopy, vol. 48, Issue 6, Jun. 1992, p. 843-848.
R. Sato, K. Kudo, T. Nagasawa, H. Suto, and K. Mizushima, "Simulations and Experiments Toward High-Data-Transfer-Rate Readers Composed of a Spin-Torque Oscillator," IEEE Transactions On Magnetics, vol. 48, 1758, 2012.
Rabehi, A., Electromagnetic microsystem for the detection of magnetic nanoparticles in a microfluidic structure for immunoassays (Doctoral dissertation). Jan. 29, 2020.
Rauwerdink, A. M., Giustini, A. J., & Weaver, J. B. (2010). Simultaneous quantification of multiple magnetic nanoparticles. Nanotechnology, 21(45), 455101.
Riedinger, A., Guardia, P., Curcio, A., Garcia, M. A., Cingolani, R., Manna, L., & Pellegrino, T. (2013). Subnanometer local temperature probing and remotely controlled drug release based on azo-functionalized iron oxide nanoparticles. Nano letters, 13(6), 2399-2406.
S. Dutz and R. Hergt, "Magnetic nanoparticle heating and heat transfer on a microscale: Basic principles, realities and physical limitations of hyperthermia for tumour therapy," Int J Hyperthermia, 2013; 29(8): 790-800.
S.I. Kiselev et al., "Microwave oscillations of a nanomagnet driven by a spin-polarized current," Nature 425, pp. 380-383, 2003.
Srimani T. et al., "High Sensitivity Biosensor using Injection Locked Spin Torque Nano-Oscillators," arXiv:1511.09072, Nov. 2015.
T. Nagasawa et al., "Delay detection of frequency modulation signal from a spin-torque oscillator under a nanosecond-pulsed magnetic field," Journal of Applied Physics, vol. 111, 07C908 (2012).
Tang, C., He, Z., Liu, H., Xu, Y., Huang, H., Yang, G., . . . & Chen, Z. (2020). Application of magnetic nanoparticles in nucleic acid detection. Journal of Nanobiotechnology, 18, 1-19. Apr. 21, 2020.
W. Andrä et al., "Temperature distribution as function of time around a small spherical heat source of local magnetic hyperthermia," Journal of Magnetism and Magnetic Materials, vol. 194, Issues 1-3, Apr. 1999, pp. 197-203.
Wang, W., & Jiang, Z., "Thermally assisted magnetic tunneling junction for biosensing applications," IEEE Transactions on Magnetics, 43(6), 2406-2408, Jun. 30, 2007.
Weifeng Shen et al., "Detection of DNA labeled with magnetic nanoparticles using MgO-based magnetic tunnel junction sensors," Journal of Applied Physics 103, 07A306 (2008).
Weijun Zhou, et al., "Novel dual fluorescence temperature-sensitive chameleon DNA-templated nanocluster pair for intracellular thermometry" Nano Research (2018), vol. 11, pp. 2012-2023, Mar. 19, 2018, https://doi.org/10.1007/s12274-017-1817-7 Mar. 19, 2018 (Mar. 19, 2018).
Xia, Haiyan et al., "Micromagnetic simulation for detection of magnetic nanobeads by spin torque oscillator," Journal of Magnetism and Magnetic Materials 2017, vol. 432, pp. 387-390, Feb. 4, 2017.

(56) References Cited

OTHER PUBLICATIONS

Y.-C. Liang, L. Chang, W. Qiu, A. G. Kolhatkar, B. Vu, K. Kourentzi, T. R. Lee, Y. Zu, R. Willson, and D. Litvinov, "Ultrasensitive Magnetic Nanoparticle Detector for Biosensor Applications," Sensors, vol. 17, 1296, 2017.
Ye, F., Zhao, Y., El-Sayed, R., Muhammed, M., & Hassan, M. (2018). Advances in nanotechnology for cancer biomarkers. Nano Today, 18, 103-123.
Yu, L., Liu, J., Wu, K., Klein, T., Jiang, Y., & Wang, J. P. (2014). Evaluation of hyperthermia of magnetic nanoparticles by dehydrating DNA. Scientific reports, 4, 7216.
Hanqiao Zhang et al., "Broadband Mag-Noise of Patterned Permalloy Thin Films," IEEE Trans. on Magnetics, vol. 46, No. 6, Jun. 2010, pp. 2442-2445.

\* cited by examiner

THERMAL SENSOR ARRAY FOR MOLECULE DETECTION AND RELATED DETECTION SCHEMES

CROSS-REFERENCE TO RELATED APPLICATIONS

This application is a divisional of U.S. application Ser. No. 16/697,013, filed Nov. 26, 2019 and entitled "THERMAL SENSOR ARRAY FOR MOLECULE DETECTION AND RELATED DETECTION SCHEMES". U.S. application Ser. No. 16/697,013 claims the benefit of U.S. Provisional Application No. 62/833,222, filed Apr. 12, 2019 and entitled "THERMOMETER ELEMENTS FOR NUCLEIC ACID SEQUENCING ARRAYS AND DETECTION SCHEMES USING HEATING OF MAGNETIC NANOPARTICLES FOR NUCLEIC ACID SEQUENCING". Both of the above-referenced applications are hereby incorporated by reference in their entireties for all purposes.

BACKGROUND

Field of the Disclosure

Embodiments of the present disclosure generally relate to temperature sensor arrays for detection of molecules coupled to magnetic nanoparticles (MNPs), such as for nucleic acid sequencing such as deoxyribonucleic acid (DNA) sequencing, and methods of using such temperature sensor arrays for molecule detection.

Description of the Related Art

Current state-of-the-art sequencing systems are based on fluorescence signal detection and provide throughputs of 20 billion reads per run (www.illumina.com/systems/sequencing-platforms/novaseq.html). Achieving such performance, however, can require large-area flow cells, high-precision free-space imaging optics, and expensive high-power lasers to generate sufficient fluorescence signals for successful base detection.

One type of nucleic acid sequencing used for DNA sequencing is known as "sequencing by synthesis" (SBS). SBS involves binding of primer-hybridized template DNA, incorporation of a deoxynucleoside triphosphate (dNTP), and detection of incorporated dNTP. Gradual increases in SBS throughput have been accomplished in two ways, the first being an outward scaling, where the size and the number of flow cells in the sequencers is increased. This approach increases both the cost of reagents and the price of the sequencing system, as more high-power lasers and high-precision nano-positioners must be employed. The second approach involves inward scaling, where the density of DNA testing sites is increased so that the total number of sequenced DNA strands in a fixed-size flow cell is higher. To accomplish inward scaling, increasingly higher numerical aperture (NA) lenses must be employed to distinguish the signal from neighboring fluorophores as the spacing between them decreases. However, this approach cannot be implemented indefinitely, as the Rayleigh criterion puts the distance between resolvable light point sources at 0.61 $\lambda$/NA, constraining the minimum distance between two sequenced DNA strands to be no smaller than approximately 400 nm. Similar resolution limits apply to sequencing directly on top of imaging arrays (similar to cell phone cameras), where the smallest pixel size achieved so far is approximately 1 (www.ephotozine.com/article/complete-guide-to-image-sensor-pixel-size-29652).

The Rayleigh criterion currently represents the fundamental limitation for inward scaling of optical SBS systems, which can only be overcome by applying super-resolution imaging techniques (see A. M. Sydor, K. J. Czymmek, E. M. Puchner, and V. Mannella, "Super-Resolution Microscopy: From Single Molecules to Supramolecular Assemblies," Special Issue: Quantitative Cell Biology, Vol. 25, 730, 2015) and has not yet been achieved in highly multiplexed systems. Hence, increasing throughput and decreasing cost of optical SBS sequencers has been slow due to the need to build bigger flow cells and implement more expensive optical scanning and imaging systems.

Therefore, there is a need for new and improved apparatuses for and methods of detecting the presence of molecules such as nucleic acids that overcome the limitations of conventional apparatuses and methods.

SUMMARY

This summary represents non-limiting embodiments of the disclosure.

In some embodiments, a detection device comprises at least one fluidic channel configured to receive a plurality of molecules to be detected, a plurality of temperature sensors, and an insulating material encapsulating the plurality of temperature sensors and for providing a barrier between the plurality of temperature sensors and contents of the at least one fluidic channel. In some such embodiments, a surface of the insulating material within the fluidic channel provides a plurality of sites for binding the plurality of molecules to be detected, the plurality of sites being located among the plurality of temperature sensors, and each of the plurality of temperature sensors is configured to detect, in the presence of an alternating magnetic field, a temperature change (e.g., in the vicinity of the temperature sensor) indicating the presence or the absence of one or more magnetic nanoparticles (MNPs) coupled to at least one of the plurality of molecules to be detected at a respective subset of the plurality of sites.

In some embodiments, each of the plurality of temperature sensors comprises a bi-metal sensing junction. In some embodiments, each of the plurality of temperature sensors comprises vanadium oxide. In some such embodiments, the vanadium oxide comprises a dopant (e.g., chromium, niobium, tungsten, iron).

In some embodiments, each of the plurality of temperature sensors comprises a nanoscale thermometer. In some embodiments, the plurality of temperature sensors comprises a thermocouple, a thermistor, a metal resistor, a bi-metal sensing junction (e.g., sensor made of two strips of dissimilar metal bonded into one element), or a tunnel junction. In some embodiments in which the plurality of temperature sensors comprises a tunnel junction, the tunnel junction comprises an insulator layer (e.g., comprising an oxide and/or a nitride) disposed between two conducting metal layers (e.g., comprising platinum, tantalum, tungsten, copper, and/or titanium).

In some embodiments, the detection device is a sequencing device, and wherein the plurality of molecules to be detected includes biologic molecules (e.g., nucleic acid molecules).

In some embodiments, the detection device further comprises detection circuitry comprising a plurality of selector devices, each of the plurality of selector devices coupled to a respective one of the plurality of temperature sensors. In some such embodiments, at least one of the plurality of selector devices comprises a transistor or an in-stack selector.

In some embodiments, a first subset of the plurality of temperature sensors is arranged in a first row, a second subset of the plurality of temperature sensors is arranged in a second row, the second row being substantially parallel to the first row, and the at least one fluidic channel is disposed between the first and second rows.

In some embodiments, the detection device further comprises detection circuitry coupled to each of the plurality of temperature sensors. In some such embodiments, the detection circuitry comprises (a) a first line coupled to a first end of each of a first subset of the plurality of temperature sensors, the first subset comprising a first temperature sensor, and (b) a second line coupled to a second end of each of a second subset of the plurality of temperature sensors, the second subset including the first temperature sensor. In some such embodiments, the first temperature sensor is the only temperature sensor of the plurality of temperature sensors that is included in both the first and second subsets. In some embodiments, a method of using this detection device comprises subjecting the detection device to the alternating magnetic field, and detecting a temperature of the first temperature sensor using the first and second lines.

In some embodiments, the detection device further comprises detection circuitry coupled to and configured to read a respective temperature of each of the plurality of temperature sensors by detecting one or more of a resistance, current, or voltage, or a change in the resistance, current, or voltage, across each of the plurality of sensors. In some such embodiments, the detection circuitry comprises at least a portion of a bridge circuit.

In some embodiments, the detection device further comprises at least one temperature control element for setting a temperature of at least a portion of the plurality of temperature sensors or the contents of the fluidic channel. In some such embodiments, the at least one temperature control element comprises at least one heater.

In some embodiments, a detection device comprises at least one fluidic channel configured to receive a plurality of molecules to be detected, a plurality of temperature sensors disposed in a cross-point array, and an insulating material disposed between the plurality of temperature sensors and contents of the at least one fluidic channel. In some such embodiments, a surface of the insulating material within the fluidic channel provides a plurality of sites located among the plurality of temperature sensors for binding the plurality of molecules to be detected, and each of the plurality of temperature sensors is configured to detect, in the presence of an alternating magnetic field, a temperature change indicating the presence or the absence of one or more magnetic nanoparticles (MNPs) coupled to at least one of the plurality of molecules to be detected at a respective subset of the plurality of sites.

In some embodiments in which the plurality of temperature sensors is disposed in a cross-point array, the cross-point array comprises a first top line, a second top line, a first bottom line, and a second bottom line, wherein the first top line is coupled to the first bottom line at a first location, the first top line is coupled to the second bottom line at a second location, the second top line is coupled to the first bottom line at a third location, and the second top line is coupled to the second bottom line at a fourth location. In some such embodiments, the first and second top lines are substantially parallel to each other, the first and second bottom lines are substantially parallel to each other, and the first and second top lines are substantially perpendicular to the first and second bottom lines. In some embodiments, the first top line is in contact with the first bottom line at the first location, thereby forming a first temperature sensor of the plurality of temperature sensors; the first top line is in contact with the second bottom line at the second location, thereby forming a second temperature sensor of the plurality of temperature sensors; the second top line is in contact with the first bottom line at the third location, thereby forming a third temperature sensor of the plurality of temperature sensors; and the second top line is in contact with the second bottom line at the fourth location, thereby forming a fourth temperature sensor of the plurality of temperature sensors.

In some embodiments having first and second top lines and first and second bottom lines, the first and second top lines comprise a first metal, and the first and second bottom lines comprise a second metal. In some such embodiments, the first metal is platinum and the second metal is tungsten, or vice versa.

In some embodiments having first and second top lines and first and second bottom lines, the first top line is coupled to the first bottom line at the first location through a first portion of insulator material, thereby forming a first temperature sensor of the plurality of temperature sensors; the first top line is coupled to the second bottom line at the second location through a second portion of the insulator material, thereby forming a second temperature sensor of the plurality of temperature sensors; the second top line is coupled to the first bottom line at the third location through a third portion of the insulator material, thereby forming a third temperature sensor of the plurality of temperature sensors; and the second top line is coupled to the second bottom line at the fourth location through a fourth portion of the insulator material, thereby forming a fourth temperature sensor of the plurality of temperature sensors. In some such embodiments, the first and second top lines comprise at least one of platinum, tungsten, tantalum, copper, or titanium; the first and second bottom lines comprise at least one of platinum, tungsten, tantalum, copper, or titanium; and the insulator material comprises at least one of an oxide or a nitride.

Some embodiments are of a method of using a detection device comprising a plurality of temperature sensors and a fluidic channel having a surface for binding molecules for detection by the plurality of temperature sensors. In some embodiments, the method comprise adding a plurality of molecules to be detected to the fluidic channel of the detection device, wherein at least some of the plurality of molecules to be detected are coupled to a first type of magnetic nanoparticle (MNP), applying an alternating magnetic field to the detection device, obtaining a temperature or temperature change at at least one temperature sensor of the plurality of temperature sensors, and, for the at least one temperature sensor of the plurality of temperature sensors, detecting, based on the obtained temperature, the presence or absence of the first type of MNP (e.g., in a vicinity of the at least one temperature sensor). In some such embodiments, the method further comprises, in response to detecting the presence of the first type of MNP (e.g., in the vicinity of the at least one temperature sensor), recording, in a record, an identity of at least one of the plurality of molecules to be detected.

In some embodiments, the method further comprises heating or cooling an environment of the plurality of temperature sensors such that each of the plurality of temperature sensors is at a substantially same temperature, the substantially same temperature selected to achieve a target temperature sensitivity of the plurality of temperature sensors, and obtaining the temperature or temperature change at the at least one temperature sensor of the plurality of temperature sensors comprises performing a temperature measurement while each of the plurality of temperature sensors is at the substantially same temperature. In some such embodiments, heating or cooling the environment of the plurality of temperature sensors comprises one or more of heating or cooling a fluid containing the plurality of molecules to be detected, heating or cooling the detection device, or heating or cooling an environment of the detection device. In some embodiments, heating or cooling the environment of the plurality of temperature sensors comprises applying a voltage or current to each temperature sensor of the plurality of temperature sensors.

In some embodiments, a detection system comprises at least one fluidic channel configured to receive a plurality of molecules to be detected, a plurality of temperature sensors, an insulating material encapsulating the plurality of temperature sensors and for providing a barrier between the plurality of temperature sensors and contents of the at least one fluidic channel, and one or more magnetic components configured to subject the contents of the at least one fluidic channel to an alternating magnetic field. In some such embodiments, a surface of the insulating material within the fluidic channel provides a plurality of sites located among the plurality of temperature sensors for binding the plurality of molecules to be detected, and each of the plurality of temperature sensors is configured to detect, in the presence of the alternating magnetic field, a temperature or temperature change indicating the presence or absence of one or more magnetic nanoparticles (MNPs) coupled to at least one of the plurality of molecules to be detected at a respective subset of the plurality of sites. In some such embodiments, the one or more magnetic components comprise an electromagnet, a distributed coil, a solenoid, a permanent magnet, or a super-conducting magnet.

In some embodiments, the detection system further comprises an alternating current (AC) current driver, and the at least one of the one or more magnetic components comprises an AC magnetic coil coupled to the AC current driver and to each of the plurality of temperature sensors. In some embodiments, the one or more magnetic components are configured to provide a static magnetic field to align respective magnetic moments of respective MNPs in a substantially same direction.

In some embodiments, a method of using the detection system comprises subjecting the contents of the fluidic channel to the alternating magnetic field, and detecting the temperature or temperature change at each of the plurality of temperature sensors.

BRIEF DESCRIPTION OF THE DRAWINGS

So that the manner in which the above-recited features of the present disclosure can be understood in detail, a more particular description of the disclosure is provided in reference to embodiments, some of which are illustrated in the appended drawings. It is to be noted, however, that the appended drawings illustrate only typical embodiments of this disclosure and are therefore not to be considered limiting of its scope, for the disclosure may admit to other equally-effective embodiments. Objects, features, and advantages of the disclosure will be readily apparent from the following description of certain embodiments taken in conjunction with the accompanying drawings in which.

To facilitate understanding, identical reference numerals have been used, where possible, to designate identical elements that are common to the figures. It is contemplated that elements disclosed in one embodiment may be beneficially utilized on other embodiments without specific recitation.

DETAILED DESCRIPTION

Figure 1:
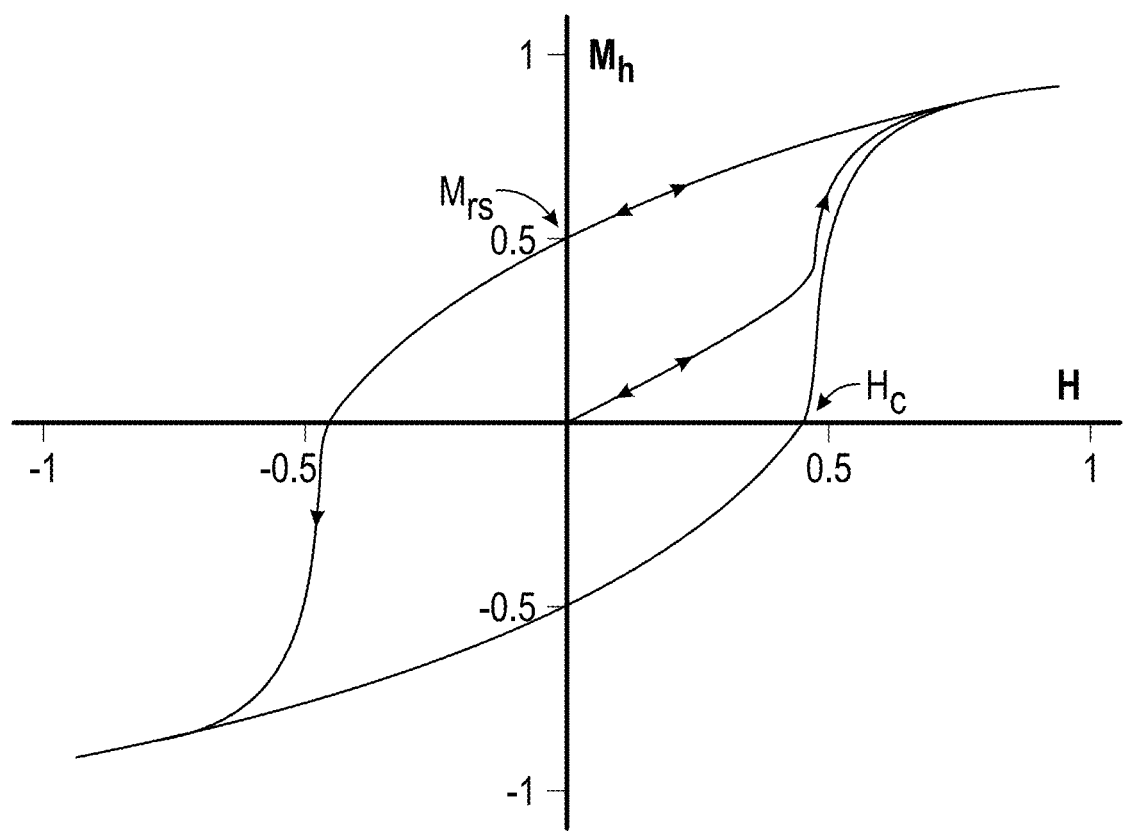
FIG. 1 is a hysteresis curve of a magnetic nanoparticle suitable for use in accordance with some embodiments.

Embodiments of the present disclosure generally relate to temperature sensor arrays for detection of molecules coupled to magnetic nanoparticles (MNPs), such as for nucleic acid sequencing such as deoxyribonucleic acid (DNA) sequencing, and methods of using such temperature sensor arrays for molecule detection. In some non-limiting examples, a DNA sequencing method may use a flow cell composed of microfluidic channels with an array of temperature sensors and sequencing chemistries using magnetic nanoparticles as identifying tags for DNA bases. The magnetic nanoparticles may be subjected to an alternating magnetic field and the magnetic nanoparticles may be magnetically heated due to relaxation losses. Some of the relaxation losses can be detected by temperature sensors to identify whether a particular molecule (e.g., a base) has been incorporated with a target DNA strand.

Electrical detection methods for nucleic acid (e.g., DNA) sequencing, as disclosed herein, have several over conventional technologies involving optical detection methods. For example, methods involving electrical detection are, at least, not limited in terms of scaling flow cell dimensions in the same manner that optical detection is limited due to optical imaging being diffraction-limited. In addition, in nucleic acid sequencing applications, electrical detection can enable for simultaneous detection of all four bases using MNPs that, when exposed to an alternating magnetic field, cause distinguishable changes in the local temperature. Thus, a single base in the target DNA strand can be read using only one chemistry step. For at least the reason that individual chemistry steps can take times on the order of minutes, the approaches disclosed herein can significantly speed up sequencing without reducing the read error rates.

In this disclosure, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative. Likewise, reference to "the disclosure" shall not be construed as a generalization of any inventive subject matter disclosed herein.

The terms "over," "under," "between," "on," and other similar terms as used herein refer to a relative position of one layer with respect to other layers. As such, for example, one layer disposed over or under another layer may be directly in contact with the other layer or may have one or more intervening layers. Moreover, one layer disposed between layers may be directly in contact with the two layers or may have one or more intervening layers. In contrast, a first layer "on" a second layer is in contact with the second layer. The relative position of the terms does not define or limit the layers to a vector space orientation of the layers.

The term "coupled" is used herein to refer to elements that are either directly connected or connected through one or more intervening elements. For example, as explained below, a line (e.g., for selecting or reading a characteristic of a temperature sensor) may be directly connected to a temperature sensor, or it may be connected via intervening elements.

The terms "sense" and "detect" are used interchangeably herein to mean obtain information from a physical stimulus. Sensing and detecting include measuring.

The terms "alternating," "oscillating," and "AC" are used interchangeably herein when used to describe a magnetic field that varies with time. The terms "static" and "DC" are used interchangeably herein when used to describe a magnetic field that remains substantially constant with time.

As used herein, the terms "vanadium oxide" and "$VO_x$" refer to any oxide or combination of oxides of vanadium that can be used in the context. Vanadium oxide includes, for example, VO (vanadium monoxide), $VO_2$ (vanadium dioxide), $V_2O_3$ (divanadium trioxide), $V_2O_5$ (divanadium pentoxide), $V_3O_5$ (trivanadium pentoxide), $V_4O_7$ (tetravanadium septoxide), etc. Vanadium oxide may comprise a dopant, such as, for example, chromium, niobium, tungsten, or iron.

It is to be understood that the disclosures herein may be used to detect any type of molecule to which a magnetic particle can be attached. In other words, any molecule type that can be labeled by a magnetic nanoparticle may be detected using the detection devices disclosed herein. Such molecule types may be biologic molecule types, such as proteins, antibodies, etc. For example, the disclosures herein may be used to detect nucleic acids (e.g., in DNA sequencing). The disclosures herein may also be used to detect non-biologic (inorganic or non-living) molecules, such as contaminants, minerals, chemical compounds, etc. The presentation of portions of the disclosure in the context of nucleic acid sequencing is solely exemplary and is not intended to limit the scope of the present disclosure.

Furthermore, although the description herein focuses on DNA as an exemplary nucleic acid, various embodiments described can be applied to nucleic acid sequencing in general. Similarly, although SBS is used for illustrative purposes in the following description, the various embodiments are not so limited to SBS sequencing protocols (e.g., dynamic sequencing could be used instead).

Conventional nucleic acid sequencing, such as that used for DNA sequencing, typically relies on the detection of fluorescence. Specifically, fluorescence-based technologies used to differentiate between different bases in a sample (e.g., in fluorescence-based nucleic acid sequencing technologies) rely on, for example, the quality of a signal generated by a detection moiety that is associated with a particular type of nucleotide. For example, conventional fluorescent sequencing technologies utilize identifiably-distinct fluorescent moieties, each attached to one of the four nucleotides A, T, C, and G that are utilized in a sequencing reaction.

One conventional method of DNA sequencing involves adapting single-strand DNA (ssDNA) for attachment to a solid support of a sequencing apparatus and amplifying the quantity of the ssDNA using techniques such as the polymerase chain reaction to create many DNA molecules with a short leader. An oligo complementary to the short leader may then be added so that there is a short section of double-stranded DNA (dsDNA) at the leader. The double stranded portion of the bound molecule is a primer for a suitable DNA polymerase, such as, for example, Taq polymerase, which is operable at high temperatures.

The sequencing can then take one of several approaches. For example, the sequencing can use a mixture of four fluorescently-labeled 3'-blocked dNTPs (fluorescently labeled dideoxynucleotide terminators), where the fluorescent label is part of the 3'-blocking group. The fluorescent label serves as a "reversible terminator" for polymerization. Each of the NTPs is labeled by a different label (i.e., each of the A, G, C, and T nucleotides has a different label), and the different labels are distinguishable by fluorescent spectroscopy or by other optical means.

Four fluorescently-labeled nucleotide precursors can be used to sequence millions of clusters of DNA strands in parallel. DNA polymerase catalyzes the incorporation of fluorescently-labeled dNTPs into a DNA template strand during sequential cycles of DNA synthesis. In each sequencing cycle, the bound double strand DNA molecule is exposed to DNA polymerase and a mixture of the four fluorescently-labeled 3'-blocked NTPs. The polymerase adds one of the four dNTPs to the growing oligonucleotide chain (whichever dNTP is complementary to the next unpaired base in the ssDNA). The unincorporated dNTPs and other impurities that are either left unreacted or generated during the reactions are then separated from the vicinity of the support-bound DNA by washing at a temperature that prevents the free dNTPs from binding to the ssDNA but is not so high as to dehybridize the dsDNA.

Because only one of the four types of dNTP will have been added to the oligonucleotide, and the four fluorescent labels are distinguishable, the identity of the incorporated dNTP can be identified through laser excitation and imaging. Specifically, each of four filters is used to determine whether light of a particular wavelength (e.g., color) is emitted. The fluorescent label can then be enzymatically cleaved to allow the next round of incorporation. Because each base type can pair with one and only one other base type, the identity of the just-paired base in the unknown sequence of the ssDNA is known from the identity of the incorporated dNTP (which is known from the wavelength of emitted light). Thus, the base is identified directly from fluorescence measurements during each cycle.

One disadvantage of the above-described approach is that a complicated optics system is needed to filter out different wavelengths of light to detect the fluorescent labels of the incorporated dNTPs and to distinguish between the different emitted colors. Other approaches have been developed to simplify the optics system, but they are slower to sequence and require intermediate chemistry steps within each sequencing cycle. Thus, these approaches have been introduced in smaller, less expensive entry-level sequencing systems but not in higher-level systems requiring fast throughput.

Disclosed herein are improved detection systems and methods that use magnetic nanoparticles (MNPs) to allow molecules to be identified. Embodiments of this disclosure include various thermometer device embodiments used as heat detectors, and detection method embodiments designed to determine (e.g., measure or obtain) variations in temperature in response to heating from a magnetic nanoparticle label exposed to an AC magnetic field.

As explained previously, the disclosures herein may be used to detect any type of molecule (e.g., biologic, organic, inorganic, or non-living) to which a magnetic particle (e.g., a MNP) can be attached. Apparatuses and methods disclosed herein use MNPs and temperature sensors to perform detection of molecules, such as in nucleic acid sequencing (e.g., DNA sequencing using SBS chemistry methods). Specifically, embodiments of this disclosure include temperature sensors that can be used to detect localized heating caused by MNPs subjected to an alternating magnetic field. Embodiments of the present disclosure may also include various detection methods to obtain or determine (e.g., measure) characteristics of the temperature sensors (e.g., voltage, current, and/or resistance) and/or localized variations in temperature caused by MNPs in response to an applied alternating magnetic field. Knowledge of which particular molecule type (e.g., in DNA sequencing applications, the type of base) to which the particular MNP label has been attached may then be used to identify the particular molecule type (e.g., in DNA sequencing applications, the next base of the ssDNA strand).

In some embodiments, discussed in more detail below, an apparatus for molecule detection comprises an array of temperature sensors. The term "temperature sensor" is used herein to refer to an element or combination of elements that senses at least one thermal stimulus such as, for example, heat, temperature, or random kinetic energy of molecules, atoms, or smaller components of matter. Each of the temperature sensors of the temperature sensor array is capable of detecting localized heating (e.g., an absolute temperature or a temperature change) in the vicinity of the temperature sensor caused by one or more MNPs in a fluidic channel of the apparatus.

MNPs

The inventors of the present disclosure had the insight that hyperthermic heating from MNPs, caused by exposure of the MNPs to an alternating magnetic field, may be used for molecule detection (e.g., for applications such as DNA sequencing). Accordingly, some embodiments of this disclosure are directed to using MNPs as tags (which may also be referred to as labels) to enable a detection device to detect molecules (e.g., DNA bases, or more generally nucleic acid bases). When the MNPs are subjected to an alternating magnetic field, they are magnetically heated due to relaxation losses. Some of the generated heat transfers to the local environment of the MNP, and this localized heating can be detected by nearby temperature sensors to identify whether a particular molecule, tagged by the MNP, is present in the vicinity of the temperature sensor (e.g., in DNA sequencing applications, whether a particular base has incorporated with one or more target DNA strands).

The MNPs may be, for example, magnetic molecules, superparamagnetic nanoparticles, or ferromagnetic particles. The MNPs may be cleavable. For example, for nucleic-acid sequencing applications (e.g., DNA sequencing applications), nucleotide precursors to be sequenced may comprise cleavable MNPs.

In MNPs below a certain critical dimension, the unpaired core electrons throughout the lattice of the materials typically tend to align substantially parallel to one another, thereby producing what is commonly known as a single domain or "macrospin" state with a spontaneous magnetic moment (or magnetization) oriented along a direction defined by some type of anisotropy energy. When a magnetic field is applied along this preferred direction, the response of the measured particle magnetization is as shown in FIG. 1, which shows the hysteresis curve for a magnetic nanoparticle. As shown in FIG. 1, the particle moment switches the direction in which it is oriented when the magnetic field is large enough (as evidenced by the change in sign of the magnetization in the graph). The applied magnetic field at which the measured magnetization is 0 is known as the coercive field $H_c$ of the MNP, whereas the measured magnetization when the applied field is zero is known as the remanent magnetization $M_{rs}$. For large enough positive and negative field values, the switching of the nanoparticle's moment generates a loop (called a hysteresis curve or loop) for which the energy loss per unit volume is $\phi H \cdot dB$ or the area contained within the hysteresis loop (as magnetization is proportional to B). From this, the specific loss power (SLP) for a MNP can be derived as:

$$SLP = \frac{4\mu_0 M_s H_c f}{\rho}$$

where $\mu_0$ is a Bohr magneton, $M_s$ is the saturation magnetization of the MNP, $H_c$ is the coercive field of the MNP (as explained above), f is the frequency of the magnetic field, and p is the density of the MNP.

For a rough estimate of the SLP value, consider a $Fe_3O_4$ MNP where $M_s$ is typically about 480 kA/m, $H_c$ is assumed to be 30 kA/m, and density is assumed to be 5240 kg/m³. When an oscillating (alternating or AC) magnetic field with frequency 500 kHz is applied, the SLP in this case is 7 kW/g (calculation obtained from Silvio Dutz and Rudolf Hergt, "Magnetic nanoparticle heating and heat transfer on a microscale: Basic principles, realities and physical limitations of hyperthermia for tumour therapy," International Journal of Hyperthermia 29, 790-800 (2013)).

In the case of superparamagnetic particles with coercive fields that are essentially 0, heating can still occur due to relaxation mechanisms such as Neel relaxation and Brownian relaxation for small-amplitude magnetic fields. Studies of hyperthermic heating from MNPs in tumors (see, e.g., W. Andrä et al., "Temperature distribution as function of time around a small spherical heat source of local magnetic hyperthermia," Journal of Magnetism and Magnetic Materials 194, 197-203 (1999)) have calculated that MNPs can generate local temperature increases in the 5-40 K range when exposed to alternating magnetic fields. For purposes of molecule detection as disclosed herein, a local temperature increase of 5-40 K can be sufficient to allow detection of heating in a particular area of a fluidic channel but does not cause the contents of the fluidic channel to reach high enough temperatures to damage biologic molecules (e.g., DNA). Various embodiments of the current disclosure take advantage of the properties of MNPs in the presence of alternating magnetic fields to detect and identify different molecules in the fluidic channel(s), such as to detect the identity of DNA bases as they incorporate into a DNA strand being sequenced.

There are a number of ways to attach the MNPs to the molecules to be detected and (if applicable) to cleave the MNPs following detection. For example, the MNPs may be attached to a base or a molecule to be detected, in which case the MNPs may be cleaved chemically. As another example, the MNPs may be attached to a phosphate, in which case the MNPs may be cleaved by, for example, polymerase or, if attached via a linker, by cleaving the linker.

In some embodiments for nucleic acid sequencing, the MNP is linked to the nitrogenous base (e.g., A, C, T, G, or a derivative) of the nucleotide precursor. After incorporation of the nucleotide precursor and detection by a detection device (e.g., as described below), the MNP may be cleaved from the incorporated nucleotide.

In some embodiments, the MNP is attached via a cleavable linker. Cleavable linkers are known in the art and have been described, e.g., in U.S. Pat. Nos. 7,057,026, 7,414,116 and continuations and improvements thereof. In some embodiments, the MNP is attached to the 5-position in pyrimidines or the 7-position in purines via a linker comprising an allyl or azido group. In some embodiments, the linker comprises a disulfide, indole, a Sieber group, a t-butyl Sieber group, and/or a dialkoxybenzyl group. The linker may further contain one or more substituents selected from alkyl (such as $C_{1-6}$) or alkoxy (such as $C_{1-6}$), nitro, cyano, fluoro groups or groups with similar properties. Briefly, the linker can be cleaved by water-soluble phosphines and/or phosphine-based transition metal-containing catalysts. Other linkers and linker cleavage mechanisms are known in the art. For example, linkers comprising trityl groups, p-alkoxybenzyl ester groups, p-alkoxybenzyl amide groups, tert-butyloxycarbonyl (Boc) groups, and acetal-based groups can be cleaved under acidic conditions by a proton-releasing cleavage agent such as an acid. A thioacetal or other sulfur-containing linker can be cleaved using a thiophilic metals, such as nickel, silver, and/or mercury. The cleavage protecting groups can also be considered for the preparation of suitable linker molecules. Ester- and disulfide containing linkers can be cleaved under reductive conditions. Linkers containing triisopropyl silane (TIPS) or t-butyldimethyl silane (TBDMS) can be cleaved in the presence of F ions. Photocleavable linkers cleaved by a wavelength that does not affect other components of the reaction mixture include linkers comprising o-nitrobenzyl groups. Linkers comprising benzyloxycarbonyl groups can be cleaved by Pd-based catalysts.

In some embodiments, the nucleotide precursor comprises a MNP label attached to a polyphosphate moiety as described in, e.g., U.S. Pat. Nos. 7,405,281 and 8,058,031. Briefly, the nucleotide precursor comprises a nucleoside moiety and a chain of 3 or more phosphate groups where one or more of the oxygen atoms are optionally substituted, e.g., with S. The label may be attached to the α, β, γ or higher phosphate group (if present) directly or via a linker. In some embodiments, the MNP label is attached to a phosphate group via a non-covalent linker as described, e.g., in U.S. Pat. No. 8,252,910. In some embodiments, the linker is a hydrocarbon selected from substituted or unsubstituted alkyl, substituted or unsubstituted heteroalkyl, substituted or unsubstituted aryl, substituted or unsubstituted heteroaryl, substituted or unsubstituted cycloalkyl, and substituted or unsubstituted heterocycloalkyl; see, e.g., U.S. Pat. No. 8,367,813. The linker may also comprise a nucleic acid strand; see, e.g., U.S. Pat. No. 9,464,107.

In embodiments in which the MNP is linked to a phosphate group, the nucleotide precursor may be incorporated into the nascent chain by the nucleic acid polymerase, which also cleaves and releases the detectable MNP. In some embodiments, the MNP is removed by cleaving the linker, e.g., as described in U.S. Pat. No. 9,587,275.

In some embodiments, the nucleotide precursors are non-extendable "terminator" nucleotides, i.e., the nucleotides that have a 3'-end blocked from addition of the next nucleotide by a blocking "terminator" group. The blocking groups are reversible terminators that can be removed in order to continue the strand synthesis process as described herein. Attaching removable blocking groups to nucleotide precursors is known in the art. See, e.g., U.S. Pat. Nos. 7,541,444, 8,071,739 and continuations and improvements thereof. Briefly, the blocking group may comprise an allyl group that can be cleaved by reacting in aqueous solution with a metal-allyl complex in the presence of phosphine or nitrogen-phosphine ligands.

Detection Methods

Some embodiments are directed to a detection device that takes advantage of magnetic hyperthermia techniques to magnetically heat MNPs coupled to molecules to be detected (e.g., dNTPs in DNA sequencing applications) and detect the presence of MNPs using temperature sensors (e.g., nanoscale temperature sensors, described in detail below) arranged to detect MNPs in a fluidic channel of a detection device. In DNA sequencing applications, as individual dNTPs are incorporated into target DNA strands present within the fluidic channel, an alternating magnetic field is applied across the fluidic channel so that the MNPs within the fluidic channel are subjected to the alternating magnetic field. As explained above, the alternating magnetic field causes the MNP tags coupled to the introduced bases to heat their surrounding areas. The temperature sensors can detect temperatures and/or changes (e.g., increases) in temperature in their vicinities and thus can indicate whether a MNP is present in the vicinity of the temperature sensors. In nucleic acid sequencing, for example, the presence or absence of a MNP can indicate whether a base labeled by that MNP has been incorporated in a DNA strand being sequenced.

The process of DNA detection may be performed in a sequential binary method in which, for example, the four nucleotide precursors (A, T, C, and G) are all labeled by the same type of MNP, and they are introduced and detected one by one. A detection step follows the introduction of each nucleotide precursor to detect whether that nucleotide precursor was incorporated. For example, a binary (yes/no, 1/0, etc.) determination may be made as to whether the magnetically-labeled nucleotide precursor being tested has been incorporated. The MNPs may then be cleaved from the incorporated sub-strand, and the next nucleotide precursor may be introduced and detected in a similar manner.

In some embodiments, instead of using a binary method with four chemistry steps for each read, either three or four different MNPs, each causing an amount of heating when subjected to an alternating magnetic field that can be distinguished from the amounts of heating caused by the other types of MNPs, can be used as the magnetic labels, and all of them can be detected in a single chemistry step. For example, each type of molecule (e.g., in DNA sequencing applications, each dNTP type) can be labeled by a different MNP type, where each MNP type causes different amounts or levels of localized heating when exposed to an alternating magnetic field that distinguishes it from the magnetic fields generated by all other MNPs being used as magnetic labels. For example, in a DNA sequencing application, A can be labeled using MNP1, T using MNP2, C using MNP3, and G either using MNP4 or left unlabeled, where the amounts of localized heating caused by MNP1, MNP2, MNP3, and (if used) MNP4 are all different enough that the three or four types of particles can be distinguished. Then all four bases can be introduced into the fluidic channel at the same time, and changes in temperature in the vicinities of temperature sensors of the detection device can be used to identify which MNP (and therefore base), if any, is incorporated in the vicinity of each temperature sensor.

Because the different MNP types coupled to different bases cause different temperature increases when exposed to the alternating magnetic field, all four bases can be detected during a single chemistry step. For example, in some embodiments, a first molecule type (e.g., adenine (A) in a DNA sequencing application) is tagged by a first MNP type that causes a first localized temperature increase in the presence of an alternating magnetic field; a second molecule type (e.g., cytosine (C) in a DNA sequencing application) is tagged by a second MNP type that causes a second localized temperature increase in the presence of the alternating magnetic field, where the second localized temperature increase is distinguishable from the first localized temperature increase; a third molecule type (e.g., guanine (G) in a DNA sequencing application) is tagged by a third MNP type that causes a third localized temperature increase in the presence of the alternating magnetic field, where the third localized temperature increase is distinguishable from the first and second localized temperature increases; and a fourth molecule type (e.g., thymine (T) in a DNA sequencing application) is tagged by a fourth MNP type that causes a fourth localized temperature increase in the presence of the alternating magnetic field, where the fourth localized temperature increase is distinguishable from the first, second, and third localized temperature increases.

For example, assume the temperature in the vicinity of each temperature sensor is expected to vary from a starting temperature in accordance with the following table in the presence of four different MNPs:

| Magnetic nanoparticle identity | Expected minimum temperature increase | Expected maximum temperature increase | Base labeled |
| --- | --- | --- | --- |
| MNP1 | $\Delta T_1$ | $\Delta T_2$ | A |
| MNP2 | $\Delta T_2$ | $\Delta T_3$ | T |
| MNP3 | $\Delta T_3$ | $\Delta T_4$ | C |
| MNP4 | $\Delta T_4$ | $\Delta T_5$ | G |

Thus, assume that $\Delta T_1 < \Delta T_2 < \Delta T_3 < \Delta T_4 < \Delta T_5$. In a DNA sequencing application, if the temperature change detected by a temperature sensor is greater than $\Delta T_2$ but less than $\Delta T_3$, it can be determined that thymine (T) was incorporated, and that the corresponding base of the DNA strand being sequenced is adenine (A).

It is to be understood that it is not necessary to use four MNPs to perform detection using a single chemistry step. For example, in some DNA sequencing embodiments, one of the bases is unlabeled. Using the example above, and assuming that guanine (G) is left unlabeled, the table becomes:

| Magnetic nanoparticle identity | Expected minimum temperature increase | Expected maximum temperature increase | Base labeled |
| --- | --- | --- | --- |
| MNP1 | $\Delta T_1$ | $\Delta T_2$ | A |
| MNP2 | $\Delta T_2$ | $\Delta T_3$ | T |
| MNP3 | $\Delta T_3$ | $\Delta T_4$ | C |
| MNP4 | 0 | 0 | G |

Relative to the example above, detection of the incorporation of A, T, and C is done as previously described, but the incorporation of G is detected by detecting that the temperature of the contents of the fluidic channel in the vicinity of a temperature sensor is approximately unchanged (e.g., it remains substantially at a starting value). Optionally, a tolerance can be used to create the detection range for the unlabeled base to account for variations in temperature in the vicinity of a temperature sensor that is not near any MNP.

After some or all temperature sensors have been addressed (e.g., accessed) and read, the magnetic field can be turned off and the MNPs may be cleaved from the incorporated magnetically-labeled nucleotide precursor using, for example, enzymatic or chemical cleavage, as is known in the art. The process can then be repeated for the next unpaired base in the strand being sequenced. For at least DNA sequencing applications, this embodiment allows for a single chemistry step per base read.

FIGS. 2A through 2D illustrate an exemplary detection process for DNA sequencing in accordance with some embodiments. In the illustrated embodiment, the sequencing process involves using multiple types of MNPs (for example, MNP types 1, 2, 3, and 4), and each base is labeled by a different MNP type. Each of the MNP types has a different SLP so that in the presence of an alternating magnetic field, each MNP type heats its local environment a different amount. As explained herein, the MNPs can be ferromagnetic or superparamagnetic. (Magnetic nanoparticles are said to be "superparamagnetic" when the loop area of their hysteresis loop, when measured under quasi-static conditions, is zero, which occurs when the nanoparticle cores are small enough to support only one magnetic domain per core, in which case they are single-domain particles.)

Figure 2A:
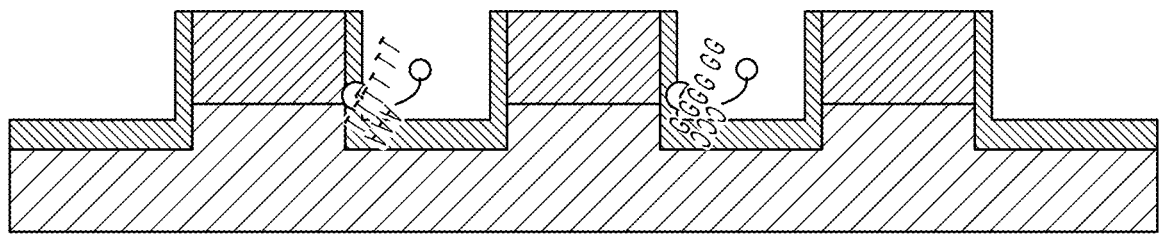
FIGS. 2A, 2B, 2C, and 2D illustrate an exemplary detection process for DNA sequencing in accordance with some embodiments.

Focusing on the DNA example for illustration, each individual base (A, T, C, G) can be labeled by a different type of MNP (e.g., base A with MNP 1, base T with MNP 2, base C with MNP 3, and base G with MNP 4) by either tagging each base separately and mixing them together or functionalizing each type of MNP differently so that it has an affinity for a particular (e.g., its assigned) base. In a single chemistry run, all tagged (labeled) bases may be introduced into a microfluidic cell (e.g., the fluidic channel of the detection device described in detail below) in which DNA strands (e.g., fragments) to be sequenced have been attached within the microfluidic cell (e.g., as described in the discussion below of the detection device). As shown in FIG. 2A, the labeled nucleotides that are complementary to the next unpaired bases in the target DNA strands are incorporated into the DNA strands. In FIG. 2A, an "A" base with MNP 1 is incorporated at one site (left portion of FIG. 2A), and a "C" base with MNP 2 is incorporated at a second site (right portion of FIG. 2A).

In some embodiments, the temperature sensors are characterized by a sensitivity that varies with temperature. Accordingly, in some embodiments, the ambient temperature (e.g., the temperature of the detection device, the temperature of the contents of the microfluidic cell, etc.) is adjusted to be at a target temperature or within a target range that corresponds to a target sensitivity (e.g., a desired sensitivity, which may be at or near a maximum known or theoretical sensitivity).

Figure 2B:
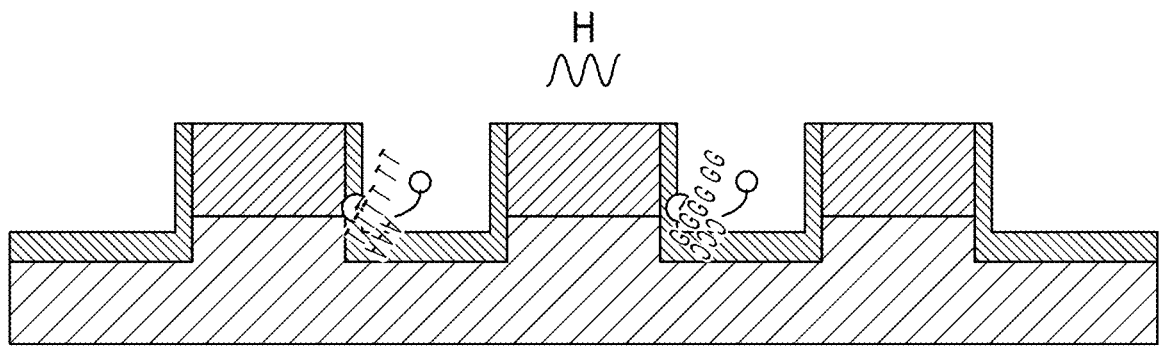

In some embodiments, as shown in FIG. 2B, an alternating (i.e., oscillating in time) magnetic field H is applied across the microfluidic cell (e.g., the fluidic channel described herein). In some embodiments, the alternating magnetic field has an amplitude of 10s or 100s of Oersteds and a frequency in the kHz to MHz range. The alternating magnetic field may be generated, for example, by an electromagnet. Optionally, a second magnet can also be used to provide a small DC (i.e., substantially constant in time) magnetic field if it is desired to orient all of the MNPs' moments in the same direction.

Figure 2C:
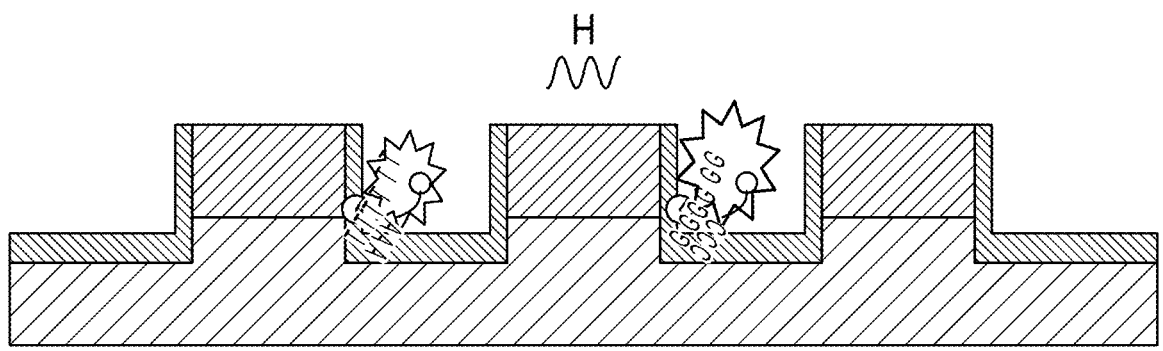

After enough time (e.g., on the order of seconds or minutes), the incorporated MNPs magnetically heat their surrounding environments, as illustrated in FIG. 2C. Because each MNP type labels a different base, and each MNP type has a different SLP, the local temperature increases will depend on which of the MNP types labels the nucleotide that has been incorporated. In the example illustrated in FIG. 2C, the MNP on the right portion of the figure heats its environment more than the MNP on the left portion of the figure heats its environment. Once the MNPs have had sufficient time to heat their local environments, some or all of the temperature sensors may be read to determine the temperatures or the temperature increases in their local areas. By analyzing the absolute temperatures or the temperature increases, the type of MNP at or near a particular site can be determined, and by extension, the base that was incorporated into the target strand can be determined.

Figure 2D:
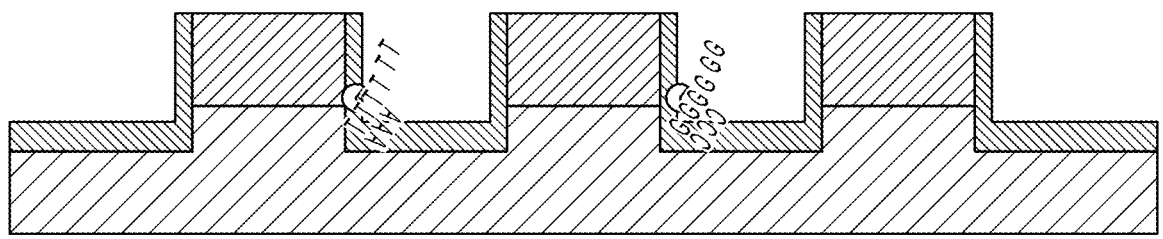

As illustrated in FIG. 2D, a chemistry step may then be run to cleave and flush the MNPs. The process can then be repeated to identify the next unpaired base in the target DNA strands. In embodiments such as the one illustrated in FIGS. 2A through 2D, the number of chemistry steps required is reduced to speed up the read process. The time required for each sequencing cycle is in part dependent on the heating time of the MNPs in the microfluidic cell.

Although FIGS. 2A through 2D illustrate an exemplary DNA sequencing embodiment in which a single chemistry step enables detection of all four bases in a single step, in other embodiments, a similar process may be performed using one type of MNP and introducing each individual base one at a time, as previously described. In such embodiments, detection may be accomplished in a binary manner, where the temperature sensors detect whether or not there is a local temperature increase indicative of the presence of the MNP type in the proximities of the temperature sensors. This method may then be repeated for the remaining bases before flushing the MNPs from the detection device and repeating the process for the next unpaired base. In some embodiments, the MNPs are cleaved prior to introducing the next nucleotide precursor to be tested so that temperature changes caused by MNPs labeling already-incorporated bases do not continue to cause localized heating. In other embodiments, the MNPs need not be cleaved prior to introducing the next nucleotide precursor to be tested. In such embodiments, the determination of whether the introduced nucleotide precursor has been incorporated can take into account the incorporation of previously-introduced nucleotide precursors (and the MNPs labeling them). Accordingly, the temperature or temperature change following introduction of a magnetically-labeled nucleotide precursor and the decision as to whether a particular nucleotide precursor labeled by a MNP has been incorporated in the target DNA strand may be dependent on the results of previous steps in the sequencing procedure.

Figure 3A:
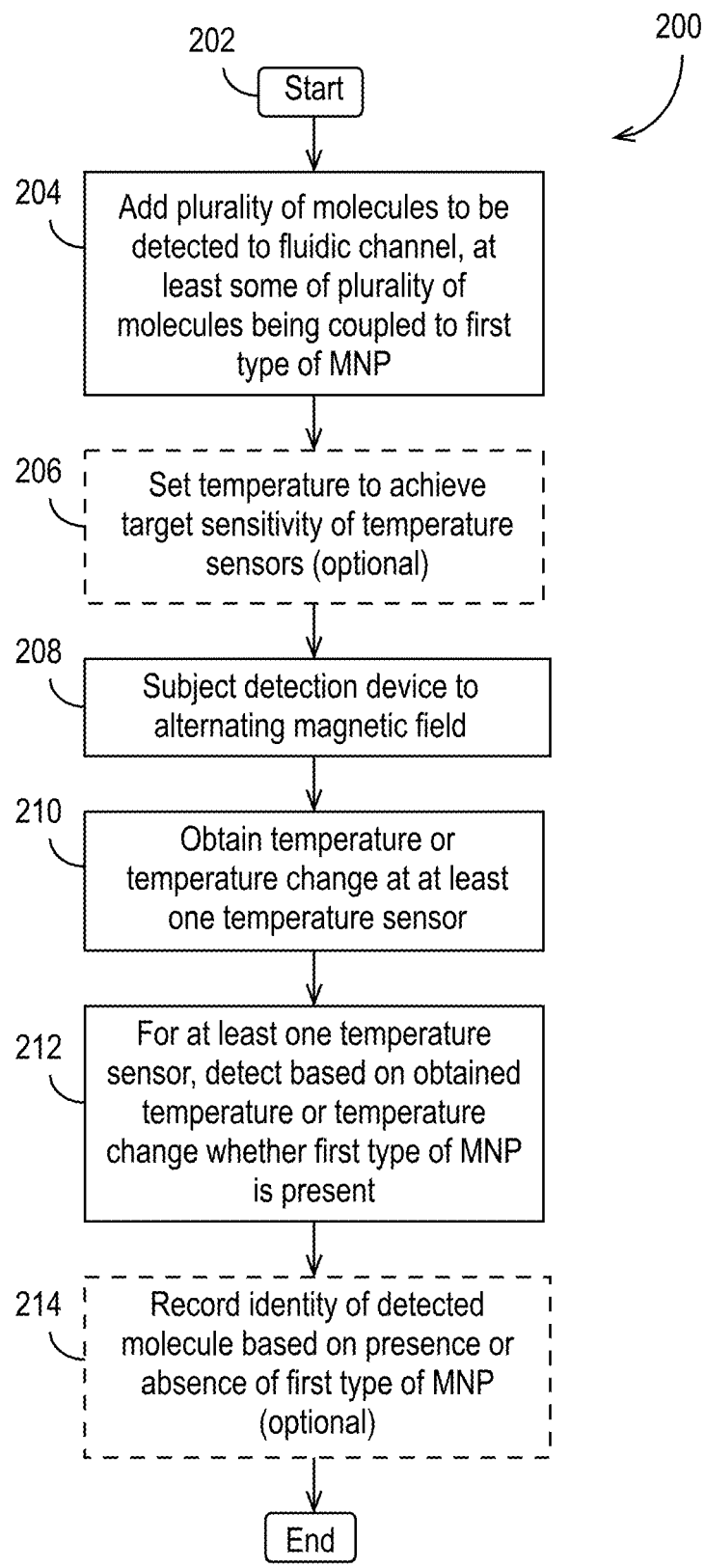
FIG. 3A is a flowchart illustrating a method for detecting molecules in accordance with some embodiments.

FIG. 3A is a flowchart illustrating a method 200 of detecting molecules (e.g., DNA bases) in accordance with some embodiments. At 202, the method begins. At 204, a plurality of molecules to be detected is added to the fluidic channel. At least some of the plurality of molecules are coupled to MNPs of a first type. Optionally, at 206, the temperature of the contents of the fluidic channel may be set to achieve a target sensitivity of the temperature sensors. At 208, an alternating magnetic field is applied to the detection device (which results in the alternating magnetic field being applied to the contents of the fluidic channel). At 210, the temperature or temperature change of the contents of the fluidic channel in the vicinity of at least one of the temperature sensors is detected (e.g., by detecting a voltage, current, and/or resistance or a change in voltage, current, and/or resistance). At 212, based on the obtained/determined (e.g., measured) temperature (or change in temperature) of at least one temperature sensor, it is determined whether the first type of MNP is present. Optionally, at 214, the identity of the detected molecule (or, in some embodiments, the identity of a complementary molecule) may be recorded based on the presence or absence of the first type of MNP in the vicinity of the temperature sensor(s).

Figure 3B:
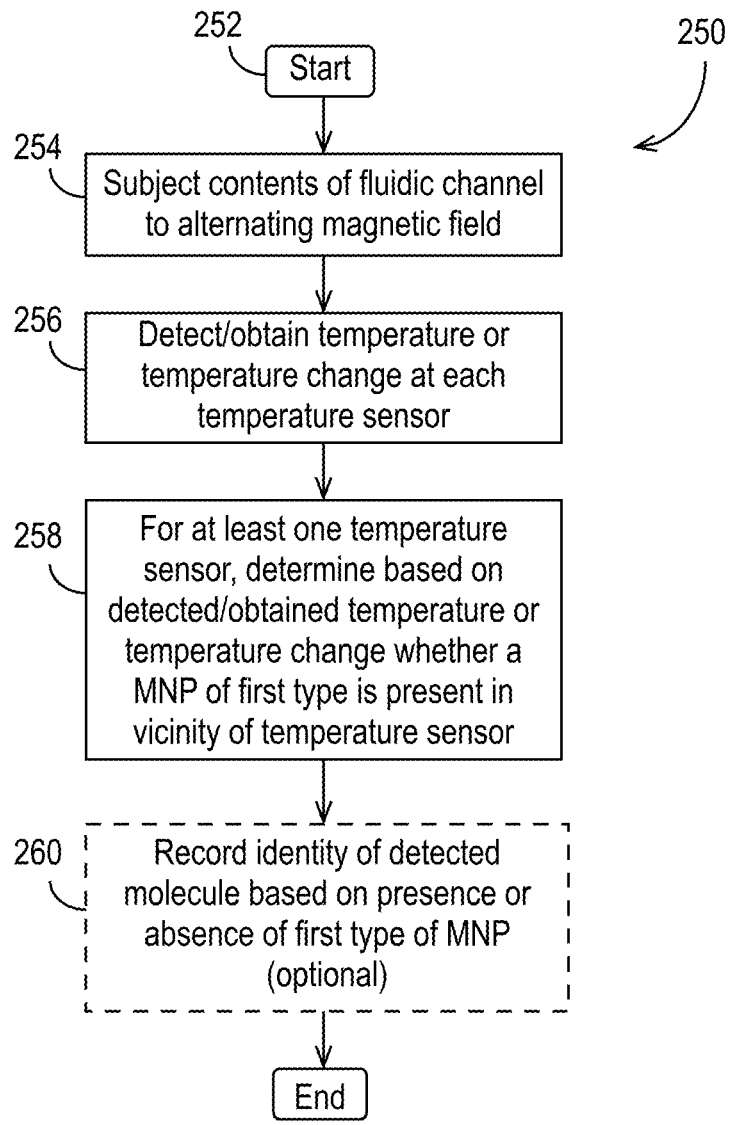
FIG. 3B is a flowchart illustrating another method for detecting molecules in accordance with some embodiments.

FIG. 3B is a flowchart illustrating another method 250 of detecting molecules in accordance with some embodiments. At 252, the method begins. At 254, the detection device is subjected to an alternating magnetic field. At 256, a local temperature change is detected at each temperature sensor. The local temperature change may be zero or close to zero (e.g., below a threshold) if there is no MNP near the temperature sensor. At 258, for at least one temperature sensor, it is determined based on the detected temperature change whether a MNP is present in the vicinity of the at least one temperature sensor. Optionally, at 260, the identity of the detected molecule may be recorded based on the presence or absence of the MNP in the vicinity of the temperature sensor(s).

Detection Devices

Figure 4A:
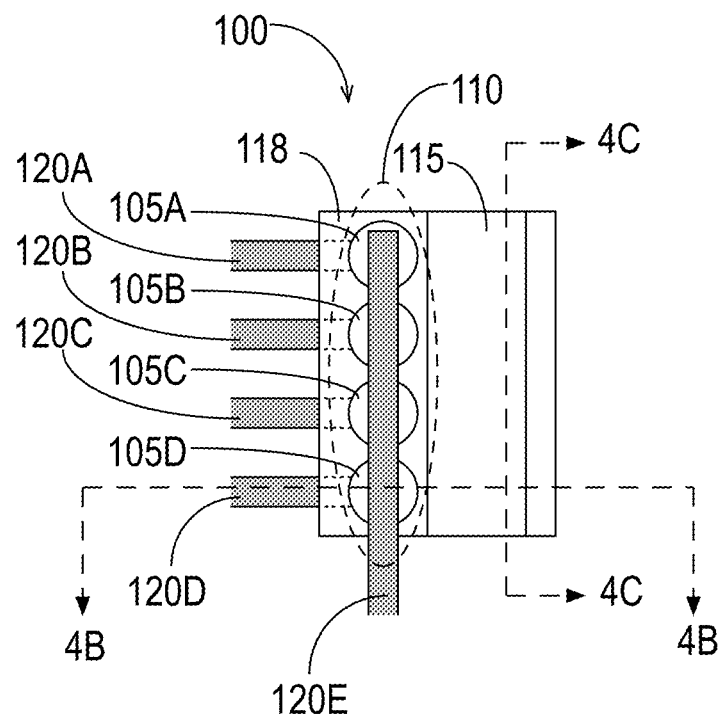
FIGS. 4A, 4B, and 4C illustrate an exemplary detection device in accordance with some embodiments.
Figure 4B:
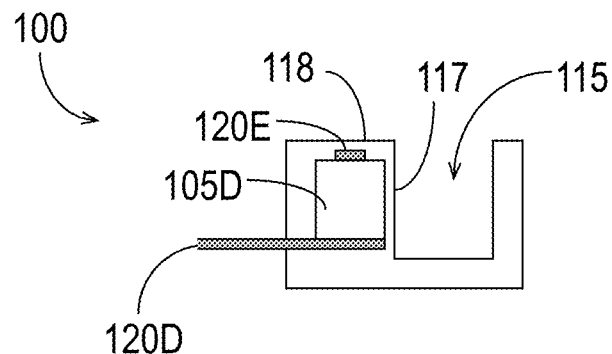
Figure 4C:
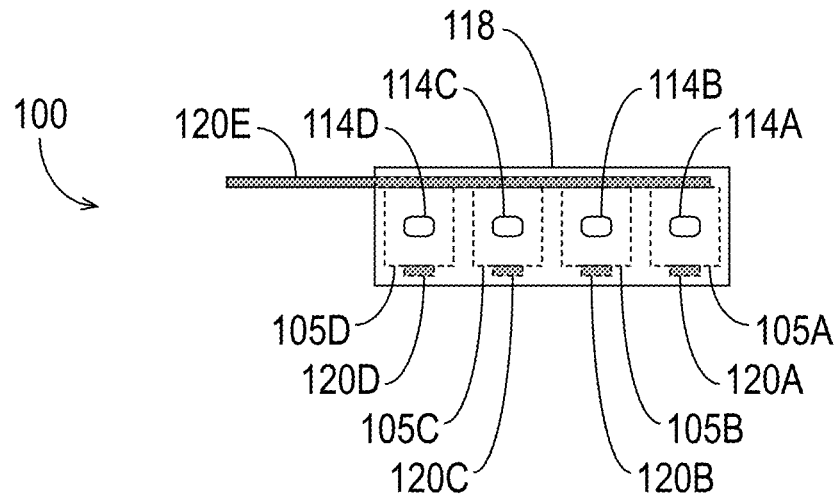

FIGS. 4A, 4B, and 4C illustrate an exemplary detection device 100 in accordance with some embodiments. The exemplary detection device 100 includes a plurality of temperature sensors 105 arranged in an array 110 disposed adjacent to a fluidic channel 115. FIG. 4A is a top view of the apparatus, FIG. 4B is a cross-section view at the position indicated by the dashed line labeled "4B" in FIG. 4A, and FIG. 4C is another cross-section view at the position indicated by the dashed line labeled "4C" in FIG. 4A. Exemplary embodiments of the temperature sensors 105 are described below (e.g., with reference to FIGS. 12, 13A, and 13B).

As shown in FIGS. 4A, 4B, and 4C, the exemplary detection device 100 comprises a temperature sensor array 110 that includes a plurality of temperature sensors 105, with four temperature sensors 105A, 105B, 105C, and 105D shown in FIG. 4A. (For simplicity, this document refers generally to the temperature sensors by the reference number 105. Individual temperature sensors are given the reference number 105 followed by a letter.) It is to be understood that the detection device 100 may include more or fewer than four temperature sensors 105. The temperature sensor array 110 illustrated in the exemplary embodiment of FIG. 4A is a linear array.

In some embodiments, each of the plurality of temperature sensors 105 is coupled to at least one line 120 for reading a characteristic of one or more of the temperature sensors 105. (For simplicity, this document refers generally to the lines by the reference number 120. Individual lines are given the reference number 120 followed by a letter.) The characteristic provides an indication of temperature or a change in temperature and may comprise, for example, a voltage, current, resistance, and/or a change in resistance, current, and/or voltage drop across the temperature sensor 105. In the exemplary embodiment shown in FIG. 4A, each temperature sensor 105 of the temperature sensor array 110 is coupled to two lines 120. Specifically, the temperature sensor 105A is coupled to the lines 120A and 120E, the temperature sensor 105B is coupled to the lines 120B and 120E, the temperature sensor 105C is coupled to the lines 120C and 120E, and the temperature sensor 105D is coupled to the lines 120D and 120E. In the exemplary embodiment, the lines 120A, 120B, 120C, and 120D reside under the temperature sensors 105A, 105B, 105C, and 105D, respectively, and the line 120E resides over the temperature sensors 105. FIG. 4B shows the temperature sensor 105D in relation to the lines 120D and 120E.

The detection device 100 also includes a fluidic channel 115 that is adjacent to the temperature sensor array 110. The fluidic channel 115 is configured to hold fluids (e.g., liquids, gases, plasmas) when the detection device 100 is in use. The fluidic channel 115 may by open (e.g., if its shape is rectangular, it may have three sides; if its shape is curved, it may have a shape that is a portion of a cylinder; etc.) or closed (e.g., if its shape is cuboid, it may have six sides; if its shape is curved, it may be cylindrical; etc.). The fluidic channel 115 may include at least one movable piece (e.g., a stopper, a flap, etc.) to allow fluid to enter into and/or exit the fluidic channel 115. The shape of the fluidic channel 115 may be regular or irregular. The fluidic channel 115 may include or may be coupled to a pump that forces fluids into and/or out of the fluidic channel 115 (e.g., through a membrane, opening, etc.). Alternatively, the fluidic channel 115 may be a passive receptacle (e.g., it merely receives fluids but is not coupled to a device that injects or removes fluids).

As shown in FIG. 4B, the fluidic channel 115 has a wall 117 that is adjacent to the temperature sensor array 110. The wall 117 may be substantially vertical as illustrated in FIG. 4B. Alternatively, the wall 117 may be sloped at least in part (e.g., some or all of the interior of the fluidic channel 115 may be curved (e.g., in the shape of a portion or all of a cylinder) or non-vertical in part or in whole). In general, the fluidic channel 115 and wall 117 may have any shapes that allow the temperature sensors 105 to detect the presence of MNPs near or attached to the wall 117, within the fluidic channel 115.

As described above, when the detection device 100 is in use, the temperature sensors 105 are able to detect temperature increases that result when MNPs that are in the fluidic channel 115 are exposed to an alternating magnetic field. Similarly, the temperature sensors 105 are able to detect temperature decreases that result when MNPs that had previously caused localized temperature increases no longer do so (e.g., when the MNPs are cleaved and washed away, or when they are not in close enough proximity to the temperature sensors 105 for any temperature increase they cause to be detected). In some embodiments, the temperature sensors 105 are able to detect absolute temperatures of contents of the fluidic channel 115 in the vicinity of the temperature sensors 105.

The wall 117 has properties and characteristics that protect the temperature sensors 105 from whatever fluid is in the fluidic channel 115 while still allowing the temperature sensors 105 to detect temperature changes in their vicinities due to localized heating caused by MNPs that are within the fluidic channel 115. For example, the material of the wall 117 (and potentially of the rest of the fluidic channel 115) may be or comprise an insulator. For example, in some embodiments, a surface of the wall 117 comprises polypropylene, gold, glass, and/or silicon. In addition, the thickness of the wall 117 may be selected so that the temperature sensors 105 can detect localized heating caused by MNPs within the fluidic channel 115. In some embodiments, the wall 117 is approximately 2 nm to approximately 20 nm thick. It may be desirable for the MNPs coupled to molecules being detected to be close to the sensors 105 but separated from them by enough insulator to electrically passivate the temperature sensors 105. The thickness of the wall 117 can be selected to meet this objective. Those having ordinary skill in the art will be able to select a suitable material and a suitable thickness of the wall 117.

FIG. 4C is a cross-section view of the detection device 100 along the dashed line labeled "4C" in FIG. 4A. Because the cross-section is taken at a point within the fluidic channel 115, the temperature sensors 105 and lines 120 would not be visible and are, therefore, shown using dashed lines to illustrate their positions within the detection device 100. As shown in FIG. 4C, in some embodiments, the wall 117 has a support structure 114 (or multiple support structures 114) configured to anchor molecules to be sensed (e.g., nucleic acid or molecules of a nucleic acid polymerase) to the wall 117 near the temperature sensors 105. FIG. 4C illustrates four individual support structures 114A, 114B, 114C, and 114D, each of which corresponds to a temperature sensor 105 (e.g., support structure 114A corresponds to temperature sensor 105A, support structure 114B corresponds to temperature sensor 105B, etc.). The support structure 114 (or support structures 114) of the wall 117 may include a cavity or a ridge to which molecules may be attached or anchored. Although FIG. 4C shows individual support structures 114 corresponding to each of the temperature sensors 105, the detection device 100 may have fewer or more support structures 114 than shown. For example, there may be more support structures 114 than temperature sensors 105, such that each temperature sensor 105 is near multiple support structures 114. As another example, multiple temperature sensors 105 may share a single support structure 114. As yet another example, multiple temperature sensors 105 may share multiple support structures 114. In embodiments in which the detection device 100 includes multiple support structures 114, those support structures 114 may be the same as or similar to each other, or they may be different from each other.

In some embodiments, it may be advantageous for each temperature sensor 105 to detect MNPs coupled to a single respective support structure 114. For example, in some types of SBS, a long strand of DNA is (or a plurality of long strands of DNA from a single donor organism are) cut into smaller, random-length segments prior to sequencing. All of these smaller strands, which are from the same donor, are randomized sub-strands of the complete strand to be sequenced. For example, if the complete strand includes the sequence ATGGCTTAG, the smaller strands could include, for example, distinct sub-strands (e.g., ATGG and TTAG) as well as, if a plurality of the longer strands are cut into sub-strands, sub-strands that partially or completely overlap other sub-strands (e.g., GGCTT and ATGGCT). All of the smaller, randomized sub-strands may be sequenced at the same time, potentially after being amplified. In such applications, it will be appreciated that because the sub-strands do not represent the same sub-sequences, it may be desirable for each temperature sensor 105 to detect temperature changes caused by single MNPs because the sequencing of the sub-strands will not be coordinated (or synchronized) amongst sub-strands. For example, during a single sequencing cycle, a first sub-strand may incorporate cytosine, a second sub-strand might incorporate thymine, and a third sub-strand might incorporate adenine. In order to sequence multiple random segments of a larger nucleic acid strand, it can be desirable, in each sequencing cycle, to determine whether and at which physical location(s) each dNTP type has been incorporated.

To simplify the explanation, FIGS. 4A, 4B, and 4C illustrate an exemplary detection device 100 with a single fluidic channel 115 and only four temperature sensors 105A, 105B, 105C, 105D in the temperature sensor array 110. It is to be appreciated that the detection device 100 may have many more temperature sensors 105 in the temperature sensor array 110, and it may have either additional fluidic channels 115 or a more intricate single fluidic channel 115 (e.g., with a different shape or with interconnected channels). In general, any configuration of temperature sensors 105 and fluidic channel(s) 115 that allows the temperature sensors 105 to detect temperature changes caused by MNPs in the fluidic channel(s) 115 may be used.

Figure 4D:
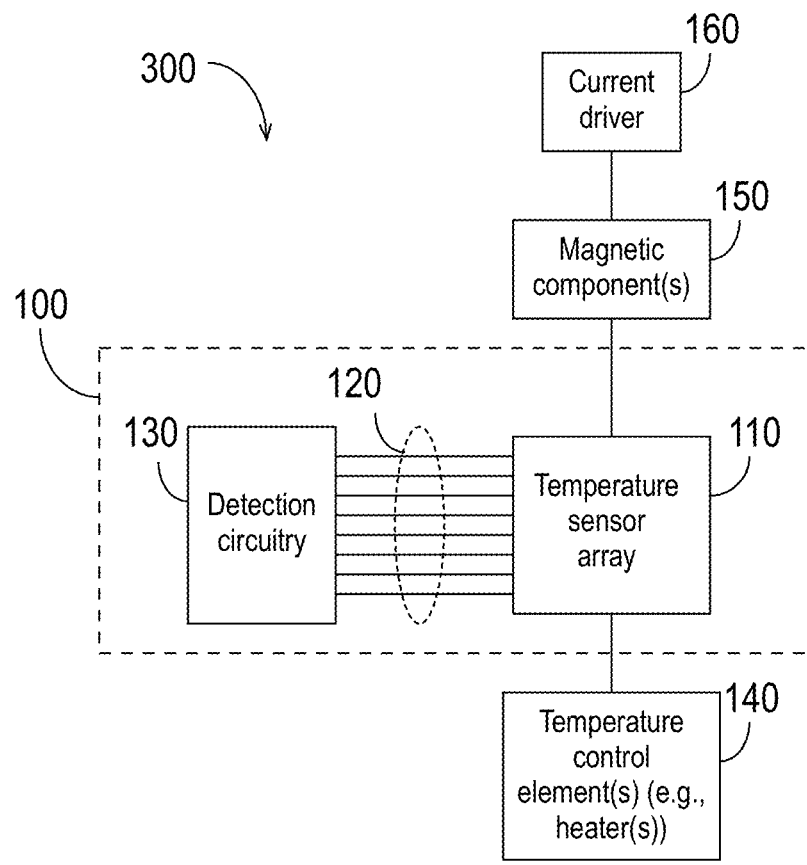
FIG. 4D is a block diagram showing an exemplary detection system for molecule detection in accordance with some embodiments.

FIG. 4D is a block diagram showing an exemplary detection system 300 for molecule detection in accordance with some embodiments. As illustrated in FIG. 4D, the system 300 includes a detection device 100 (as shown, comprising detection circuitry 130 coupled to the temperature sensor array 110 via the lines 120). As also shown in FIG. 4D, the detection system 300 may also include one or more temperature control elements 140 (e.g., one or more heaters), one or more magnetic components 150, and/or a current driver 160. The magnetic component(s) 150 may comprise, for example, an electromagnet, a distributed coil, a solenoid, a permanent magnet, or a superconducting magnet. In addition to including one or more magnetic components 150 to generate an alternating magnetic field, the magnetic component(s) 150 may include a magnetic component 150 that provides a static (e.g., constant in time or DC) magnetic field to align the magnetic moments of the MNPs in the fluidic channel 115 in substantially the same direction. Although FIG. 4D illustrates the temperature controller(s) 140, magnetic component(s) 150, and/or current driver 160 as being separate from the detection device 100, one or more of the temperature controller(s) 140, magnetic component(s) 150, and/or current driver 160, if present, may be included in the detection device 100, or some or all of the temperature controller(s) 140, magnetic component(s) 150, and/or current driver 160 may be separate from the detection device 100.

In some embodiments, in operation, the current driver 160 causes the magnetic component(s) 150 to generate an alternating magnetic field to which the contents of the fluidic channel 115 are subjected. In response to the alternating magnetic field, MNPs in the fluidic channel 115 heat their surrounding environments. The detection circuitry 130 applies a current or voltage to one or more of the lines 120 to detect a characteristic of at least one of the plurality of temperature sensors 105 in the temperature sensor array 110, where the characteristic is a proxy for temperature (or temperature change) and indicates the presence or an absence of a MNP in the fluidic channel 115. For example, in some embodiments, the characteristic is a voltage, current, and/or resistance, or a change in voltage, current, and/or resistance.

Figure 5:
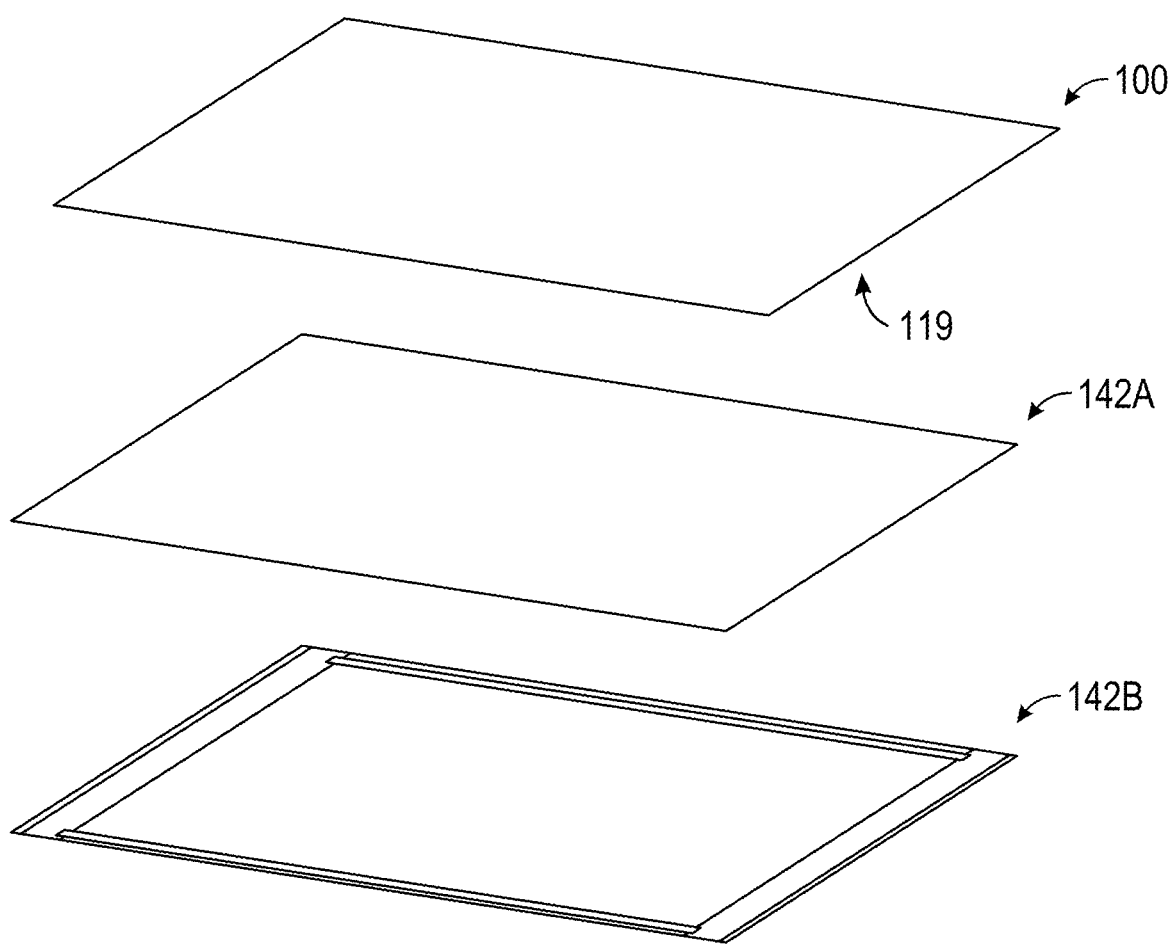
FIG. 5 illustrates heating elements of an exemplary detection device in accordance with some embodiments.

In some embodiments, the temperature sensors 105 are most sensitive in a particular temperature range. Thus, in some such embodiments, it can be desirable to keep the temperature sensors 105 within this temperature range. One way to do so is by using temperature gradient correction. Accordingly, in some embodiments, the system 300 includes one or more temperature control elements 140, which may comprise, for example, one or more heating elements. For example, the system 300 may include a heat spreader, which may be coupled to the detection device 100. In some embodiments, the detection device 100 itself includes one or more heating elements 142 coupled, for example, to its bottom surface 119. FIG. 5 is an exploded view of exemplary heating elements 142 suitable for incorporation in or use with a detection device 100 in accordance with some embodiments. The detection device 100 shown in FIG. 5 includes or is coupled to a surface heater 142A that provides substantially uniform heating across the bottom surface 119 of the detection device 100. The detection device 100 shown in FIG. 5 also includes linear heaters 142B at or near the edges of the bottom surface 119, which may be used to remove a temperature gradient caused by the surrounding environment being at a different (e.g., cooler) temperature.

Figure 6:
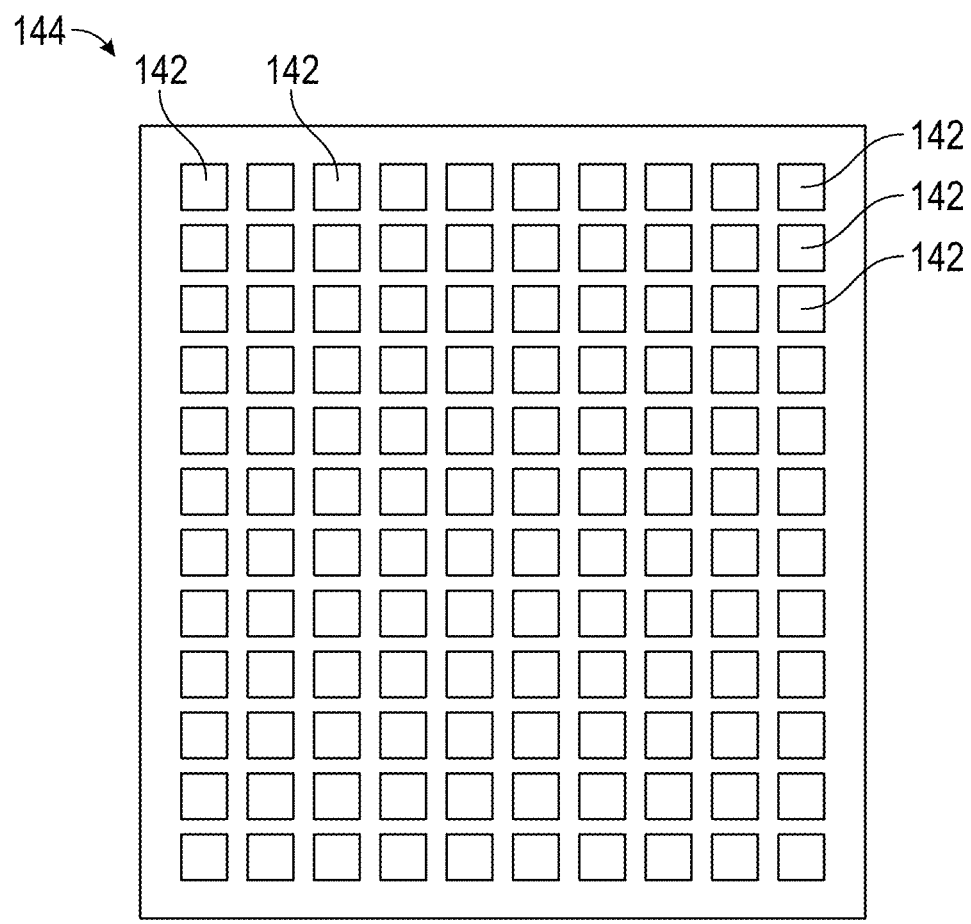
FIG. 6 illustrates an exemplary array of heating elements that may be coupled to the bottom surface of the detection device in accordance with some embodiments.

Alternatively or in addition, the detection device 100 may include an array of heating elements 142, which may be useful if fine temperature control is desirable. FIG. 6 illustrates an array 144 of heating elements 142 that may be coupled, for example, to the bottom surface 119 of the detection device 100. To avoid obscuring the drawing, only a few of the heating elements 142 are shown with reference numbers.

In some embodiments, the temperature sensors 105 are kept within a desired temperature range (e.g., to provide a desired sensitivity) by applying a current to the temperature sensors 105. For example, the temperature of a temperature sensor 105 may be obtained/determined (e.g., measured) by applying a voltage to the lines 120 coupled to that temperature sensor 105 and measuring the current, and if the temperature sensor 105 is not within the desired temperature range, its temperature can be adjusted by increasing or decreasing the applied current. In embodiments in which the lines 120 are used to control the temperatures of the temperature sensors 105, the temperature-adjustment procedure may be performed between molecule detection cycles. Alternatively, it may be performed at the same time as molecule detection. If the changes made to the current for purposes of temperature-adjustment are small, the detection circuitry 130 should still be able to detect changes in temperature caused by MNPs in the vicinities of the temperature sensors 105.

Figure 7:
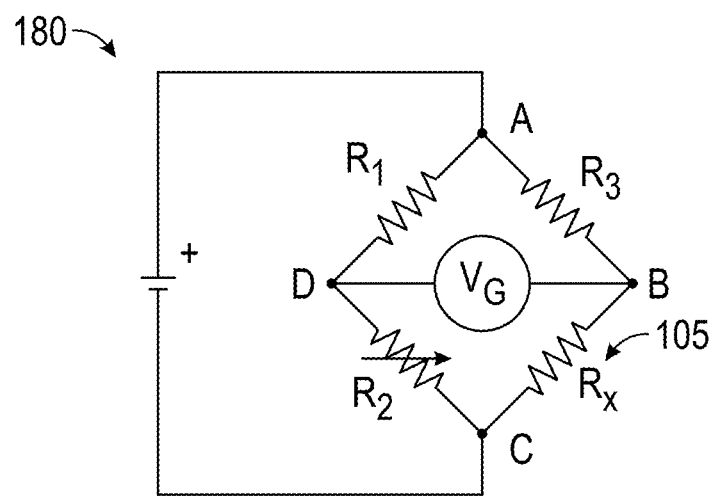
FIG. 7 illustrates an exemplary bridge circuit for use in molecule detection in accordance with some embodiments.

In some embodiments, the temperature sensors 105, which are described in further detail below, are arranged in bridge circuits, and temperature changes caused by the presence of MNPs in the fluidic channel 115 are detected through measurement of voltage changes in the bridge circuits due to resistance changes in the temperature sensors 105. FIG. 7 illustrates an exemplary bridge circuit 180 in accordance with some embodiments. The temperature sensor 105 (shown as a resistor having a resistance $R_x$) is disposed as one leg of the bridge circuit 180. The other legs of the bridge circuit 180 may be considered to be included in the detection circuitry 130. The other legs of the bridge circuit 180 may include, for example, low-temperature coefficient resistors, which may be fabricated (e.g., on the detection device 100) using the same material(s) as the temperature sensor 105 (in which case their resistances change at substantially the same rate as the resistance of the temperature sensor 105). A variable resistor (labeled $R_2$) may be used, as shown in FIG. 7, to balance the bridge.

As will be appreciated by those skilled in the art, FIG. 7 is merely exemplary, and other bridge configurations are possible. For example, the bridge circuit 180 may include two temperature sensors 105 to determine or obtain temperature changes caused by MNPs and two reference resistors to track (e.g., measure) background temperature changes. Bridge configurations with interleaved resistors (to reduce gradients) or with only two resistors are possible. The exemplary configuration of FIG. 7 is not intended to be limiting.

As an example of a detection device 100 with a larger number of temperature sensors 105 in the temperature sensor array 110, FIGS. 8A, 8B, 8C, and 8D illustrate portions of an exemplary detection device 100 that includes several fluidic channels 115, one or more of which may be a separate fluidic channel 115 in accordance with some embodiments, or the aggregation of which may be considered a single fluidic channel 115. In the embodiment of the detection device 100 shown in FIGS. 8A, 8B, 8C, and 8D, the plurality of temperature sensors 105 of the temperature sensor array 110 is arranged in a rectangular grid pattern. Each of the lines 120 identifies a row or a column of the temperature sensor array 110. It is to be understood that FIGS. 8A, 8B, 8C, and 8D show only a portion of the detection device 100 to avoid obscuring the parts of the detection device 100 being discussed. It is to be understood that the various illustrated components (e.g., lines 120, temperature sensors 105, fluidic channels 115, etc.) might not be visible in a physical instantiation of the detection device 100 (e.g., some or all may be covered by protective material, such as an insulator). Moreover, as discussed herein, the detection device 100 may include other components not illustrated in FIGS. 8A, 8B, 8C, and 8D.

Figure 8A:
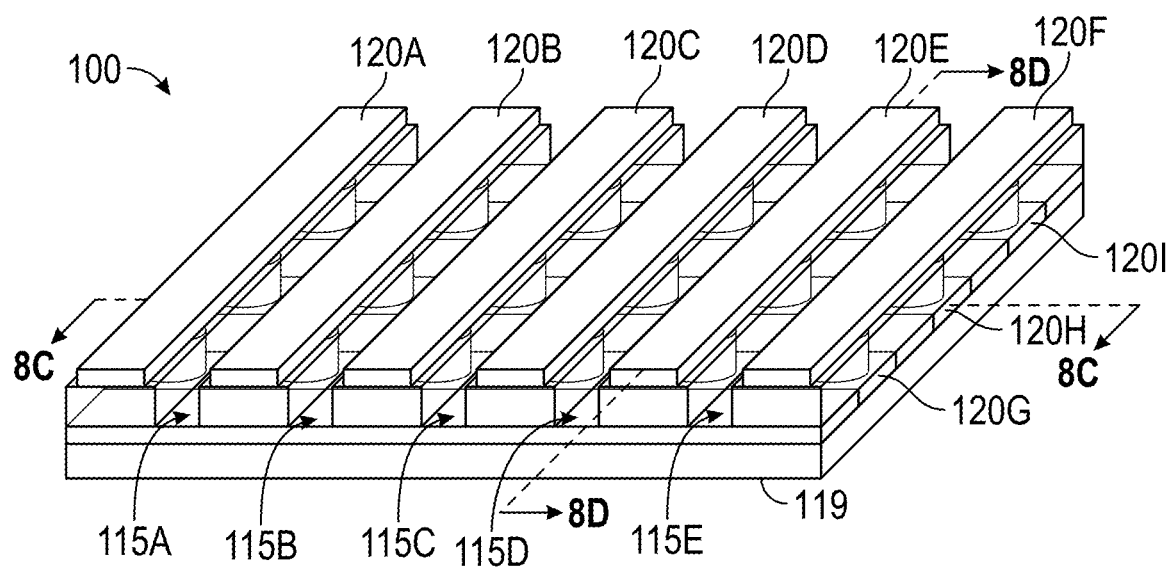
FIGS. 8A, 8B, 8C, and 8D illustrate portions of an exemplary detection device in accordance with some embodiments.

FIG. 8A is a perspective view of the exemplary detection device 100 in accordance with some embodiments. The exemplary detection device 100 includes nine lines 120, labeled as 120A, 120B, 120C, 120D, 120E, 120F, 120G, 120H, and 120I. It also includes five fluidic channels, labeled as 115A, 115B, 115C, 115D, and 115E. As explained above, the fluidic channels 115A, 115B, 115C, 115D, and 115E may be considered to be separate fluidic channels 115 or a single fluidic channel 115. The detection device 100 also has a bottom surface 119.

Figure 8B:
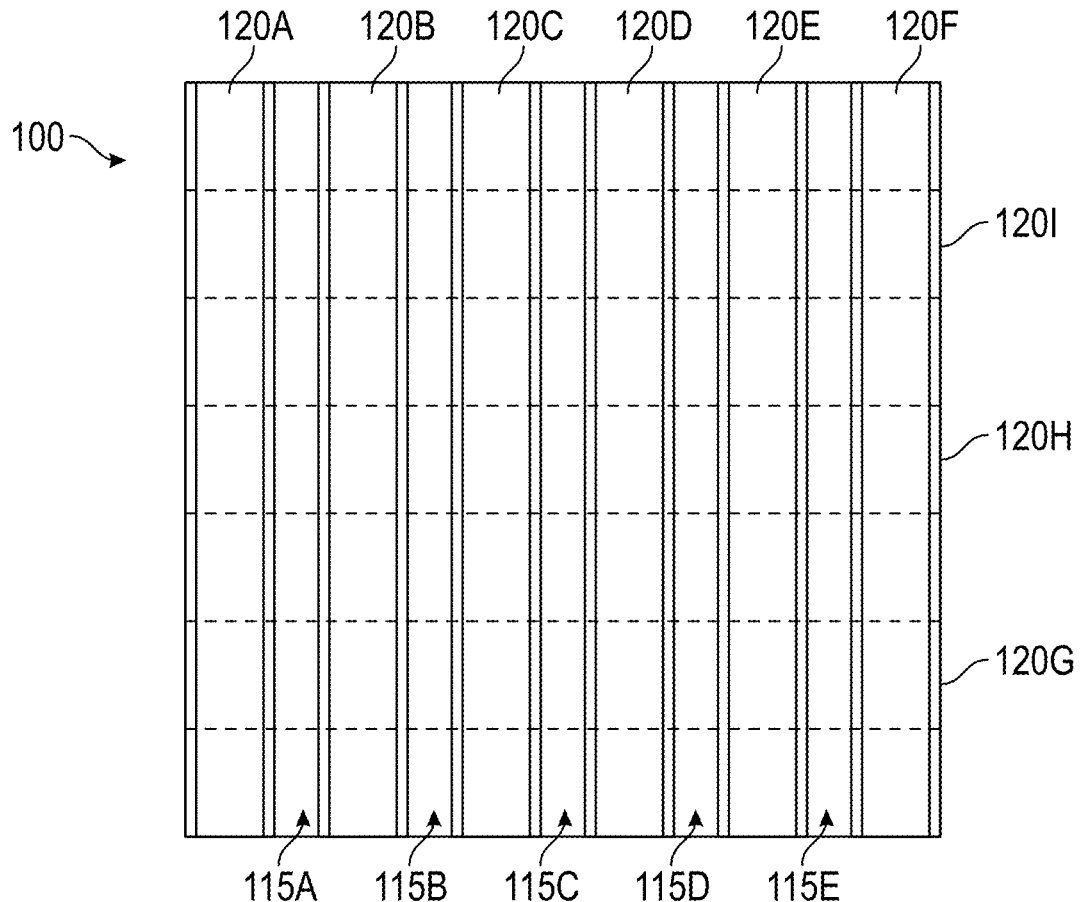

FIG. 8B is a top view of the exemplary detection device 100 shown in FIG. 8A. The lines 120G, 120H, and 120I, which are not visible from the top view, are shown using dashed lines to indicate their locations. The lines 120A-120F are shown in solid lines but, as explained above, the lines 120A-120F might also not be visible in the top view (e.g., they may be covered by protective material, such as an insulator).

Figure 8C:
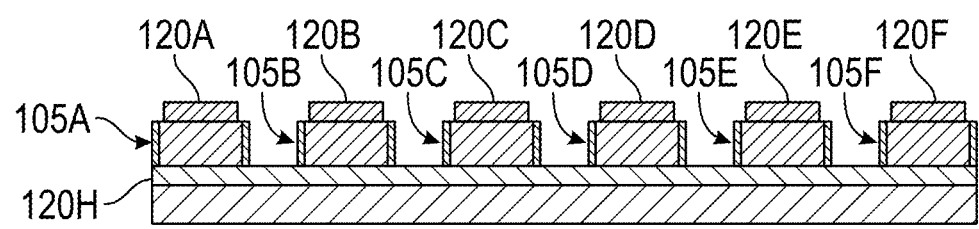

FIG. 8C is a cross-sectional view of the detection device 100 along the line labeled "8C" in FIG. 8A. As shown, each of the lines 120A, 120B, 120C, 120D, 120E, and 120F is in contact with the top of one of the temperature sensors 105 along the cross-section (namely, line 120A is in contact with temperature sensor 105A, line 120B is in contact with temperature sensor 105B, line 120C is in contact with temperature sensor 105C, line 120D is in contact with temperature sensor 105D, line 120E is in contact with temperature sensor 105E, and line 120F is in contact with temperature sensor 105F). The line 120H is in contact with the bottom of each of the temperature sensors 105A, 105B, 105C, 105D, 105E, and 105F. It is to be appreciated that although FIGS. 8A-8D illustrate the lines 120 in contact with the temperature sensors 105, the lines 120 may, in general, be coupled to the temperature sensors 105 (i.e., they may be directly connected, or there may be intervening components disposed between the lines 120 and the temperature sensors 105). Moreover, although FIGS. 8A-8D illustrate the lines 120 and temperature sensors 105 as distinct from one another, as discussed in further detail below in the context of FIGS. 13A and 13B, the lines 120 may themselves form part or all the temperature sensors 105.

Referring again to FIG. 8C, the temperature sensors 105A and 105B are separated by the fluidic channel 115A (unlabeled in FIG. 8C but shown in FIG. 8A). Similarly, the temperature sensors 105B and 105C are separated by the fluidic channel 115B, the temperature sensors 105C and 105D are separated by the fluidic channel 115C, the temperature sensors 105D and 105E are separated by the fluidic channel 115D, and the temperature sensors 105E and 105F are separated by the fluidic channel 115E. As discussed further below, either or both of the vertical walls of each fluidic channel 115 may be the wall 117.

In some embodiments, each temperature sensor 105 is assigned to a single fluidic channel 115. For example, in the exemplary device illustrated in FIGS. 8A-8D, the temperature sensors 105 coupled to the line 120A may be configured to sense the presence or absence of MNPs in the fluidic channel 115A, the temperature sensors 105 coupled to the line 120B may be configured to sense MNPs in the fluidic channel 115B, the temperature sensors 105 coupled to the line 120C may be configured to sense MNPs in the fluidic channel 115C, the temperature sensors 105 coupled to the line 120D may be configured to sense MNPs in the fluidic channel 115D, and the temperature sensors 105 coupled to the line 120E may be configured to sense MNPs in the fluidic channel 115E.

In the exemplary embodiment illustrated in FIGS. 8A-8D, there are more columns of temperature sensors 105 than there are fluidic channels 115 (i.e., in the exemplary embodiment shown, there are six columns corresponding to lines 120A-120F and only five fluidic channels 115A-115E). In such embodiments, each wall of one fluidic channel 115 may be the wall 117. In other words, a single fluidic channel 115 may be sensed by twice as many temperature sensors 105 as each of the other fluidic channels 115. For example, in the exemplary embodiment of FIGS. 8A-8D, any of the fluidic channels 115 may be sensed by two columns of temperature sensors 105. For example, the fluidic channel 115B may be sensed by the temperature sensors 105 coupled to both lines 120B and 120C. In this example, the temperature sensors 105 coupled to the line 120A would be assigned to sense the contents of the fluidic channel 120A, the temperature sensors 105 coupled to the line 120D would be assigned to sense the contents of the fluidic channel 120C, the temperature sensors 105 coupled to the line 120E would be assigned to sense the contents of the fluidic channel 120D, and the temperature sensors 105 coupled to the line 120F would be assigned to sense the contents of the fluidic channel 120E.

Figure 8D:
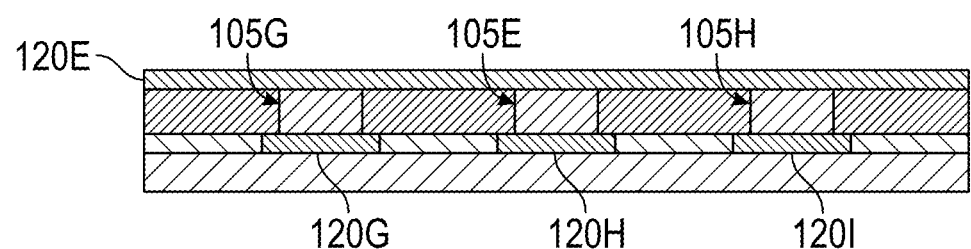

FIG. 8D is a cross-sectional view of the detection device 100 along the line labeled "8D" in FIG. 8A. As shown, the line 120E is in contact with the top of each of the sensors 105G, 105E, and 105H along the cross-section. Each of the lines 120G, 120H, and 120I is in contact with the bottom of one of the temperature sensors 105 along the cross-section (namely, line 120G is in contact with temperature sensor 105G, line 120H is in contact with temperature sensor 105E, and line 120I is in contact with temperature sensor 105H). In some embodiments, as discussed in further detail below, the temperature sensors 105 comprise vanadium oxide or a material with similar properties (e.g., niobium oxide). In some such embodiments, the lines 120 use the selectivity of the temperature sensor 105 itself to detect the temperature or change in temperature.

Figure 9A:
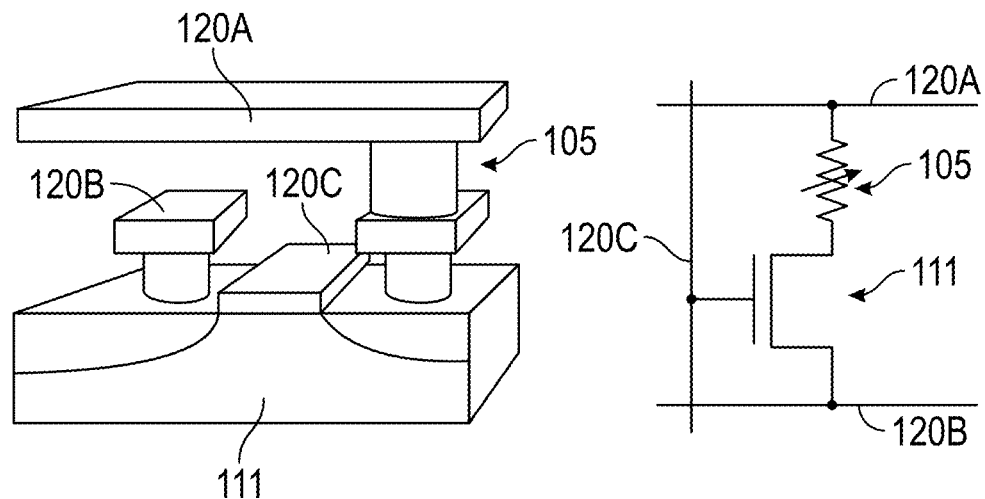
FIG. 9A illustrates an exemplary approach for selecting temperature sensors in accordance with some embodiments.
Figure 9B:
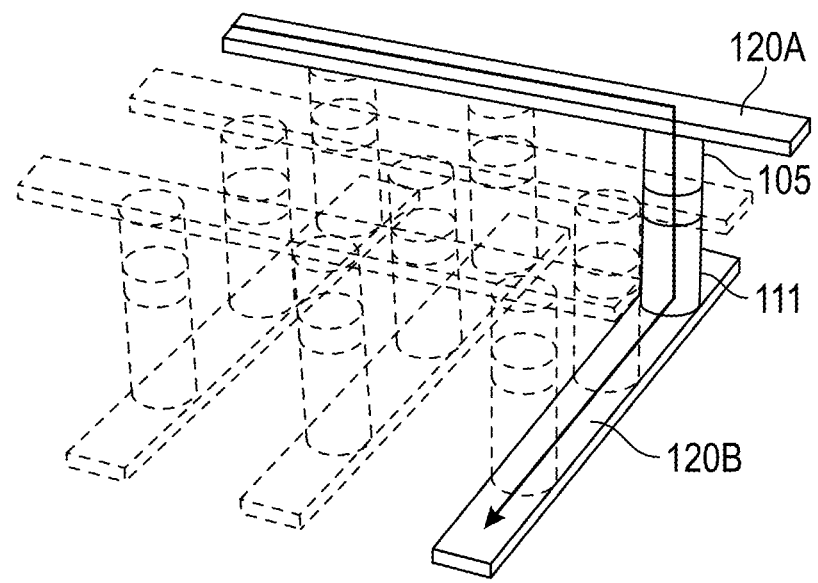
FIG. 9B illustrates another exemplary temperature sensor selection approach in accordance with some embodiments.

As explained above, the lines 120 shown in FIG. 8D need not be in direct contact with the temperature sensors 105; instead, they may be connected through intervening components. For example, in some embodiments, such as shown in FIGS. 9A and 9B, the detection device 100 includes a plurality of selector elements 111, each of which is coupled to a respective one of the temperature sensors 105, where each of the selector elements 111 exhibits thresholding behavior such that for voltages above a particular value ($V_{th}$), the selector element 111 has high conductivity, and below that voltage the conductivity of the selector element 111 is effectively zero. The selector elements 111 may comprise, for example, transistors, diodes, etc. As will be appreciated by those having ordinary skill in the art, different schemes of addressing (selecting) the temperature sensors 105 (individually or in groups) can be used that ensure only the voltage dropped across the intended temperature sensor(s) 105 is above $V_{th}$. Accordingly, selector elements 111 may be used reduce the chances of "sneak" currents that could transmit through neighboring elements and degrade the performance of the detection device 100.

FIG. 9A illustrates an exemplary approach for selecting temperature sensors 105 in accordance with some embodiments. In the exemplary embodiment shown in FIG. 9A, a respective selector element 111 (shown in the exemplary embodiment as a CMOS transistor) is coupled in series with the temperature sensor 105. In this exemplary embodiment, three lines 120A, 120B, and 120C allow a characteristic of the temperature sensor 105 to be sensed. Conceptually, the line 120A may be considered to be a read-out line, the line 120C may be considered to be a control line, and the line 120B may be considered to be either or both a read-out line and a control line. Each temperature sensor 105 of an array 110 may be coupled in series to a respective selector element 111. For more detail on configurations such as the exemplary one shown in FIG. 9A, see B. N. Engel, J. Åkerman, B. Butcher, R. W. Dave, M. DeHerrera, M. Durlam, G. Grynkewich, J. Janesky, S. V. Pietambaram, N. D. Rizzo, J. M. Slaughter, K. Smith, J. J. Sun, and S. Tehrani, "A 4-Mb Toggle MRAM Based on a Novel Bit and Switching Method," IEEE Transactions on Magnetics, Vol. 41, 132 (2005).

FIG. 9B illustrates another exemplary temperature sensor 105 selection approach in accordance with some embodiments. In the exemplary embodiment shown in FIG. 9B, a selector element 111 (e.g., a diode or a similar thresholding element, as is known in the art, such as semiconductor diodes, operational transconductance amplifiers (OTAs), vanadium oxide layers, capacitive threshold-logic gates, etc.) is deposited "in-stack" together with each of the temperature sensors 105, which are placed into a cross-point architecture. Although FIG. 9B shows the in-stack selector elements 111 under the temperature sensors 105, it is to be understood that the stacking of the in-stack selector elements 111 and the temperature sensors 105 may be reversed (i.e., the in-stack selector elements 111 may be over the temperature sensors 105). Respective selector devices (e.g., CMOS transistors) may be used to turn on the individual lines 120A, 120B to address/access individual temperature sensors 105 in the detection device 100. The use of CMOS select transistors may be simple due to the prevalence of foundries available to fabricate the front end (e.g., the nanofabrication to build the CMOS transistors and underlying circuitry), but the types of currents used for operation may use a cross-point design to eventually reach the densities desired. Additional details on configurations suitable to select temperature sensors 105 (e.g., in cross-point arrays) may be found in C. Chappert, A. Fert, and F. N. Van Daul, "The emergence of spin electronics in data storage," Nature Materials, Vol. 6, 813 (2007) and in J. Woo et al., "Selector-less RRAM with non-linearity of device for cross-point array applications," Microelectronic Engineering 109 (2013) 360-363.

In embodiments in which the temperature sensors 105 are arranged in a cross-point array, entire columns or entire rows may be read simultaneously to improve the accuracy of the detection.

As described herein, the exemplary detection device(s) 100 shown and described in reference to FIGS. 4A-9B can be used with methods using SBS protocols that use magnetically-labeled nucleotide precursors. SBS involves binding of primer-hybridized template DNA, incorporation of a deoxynucleoside triphosphate (dNTP), and detection of incorporated dNTP. The detection device 100 can be used to expose the temperature sensors 105 to sequencing reagents in the fluidic channel(s) 115 while protecting the temperature sensors 105 using, for example, an electrically-insulating material. As described herein, DNA synthesis may be performed using polymerase molecules placed in the proximity of the temperature sensors 105, which detect the presence of MNPs.

In particular, as described herein, either molecules of polymerase or fragments of single-strand nucleic acid may be attached to the side wall(s) 117 of the fluidic channel(s) 115 in the proximity of one or more of the temperature sensors 105. Sequencing can then be performed by adding, to the fluidic channel(s) 115, a nucleic acid template (having a primer binding site and an extendable primer) and magnetically-labeled nucleotide precursors (at least some types of nucleotide precursor labeled by a distinguishable MNP), and sequencing the nucleic acid template by using the lines 120 to detect a characteristic of the temperature sensors 105. The characteristic may indicate which of the magnetically-labeled nucleotide precursors has been incorporated into the extendable primer (e.g., if multiple nucleotide precursors, each labeled by a different MNP type, are added to the fluidic channel(s) 115 at substantially the same time), or it may indicate whether a particular magnetically-labeled nucleotide precursor has been incorporated into the extendable primer (e.g., if different nucleotide precursors labeled by MNPs (which may be the same type of MNP for each type of nucleotide precursor) are added to the fluidic channel(s) 115 sequentially). For DNA sequencing specifically, because adenine (A) pairs only with thymine (T), and cytosine (C) pairs only with guanine (G), detection of the MNPs enables the determination of which of the magnetically-labeled nucleotide precursors has been incorporated. In particular, if the MNP labeling A is detected, the recorded base is T (and vice versa), and if the MNP labeling C is detected, the recorded base is G (and vice versa).

Temperature Sensors

The temperature sensors 105 can have any of a number of configurations, and they may comprise a variety of suitable materials. For example, as explained further below, the temperature sensors 105 may comprise thermocouples made from two different metals (see, e.g., U.S. Pat. No. 6,905,736, "Fabrication of nano-scale temperature sensors and heaters," which is hereby incorporated by reference in its entirety for all purposes), semiconductor diodes (see, e.g., U.S. Pat. No. 6,969,679, "Fabrication of nanoscale thermoelectric devices," which is hereby incorporated by reference in its entirety for all purposes), thermistors, metal resistors, and/or tunnel junctions (magnetic or non-magnetic).

The temperature sensors 105 may comprise, for example, resistive thermal sensors. A resistive thermal sensor is a thermal sensor with an electrical resistance that varies with the thermal stimulus that it senses (where the variation in resistance can include both linear and nonlinear variations). The term "thermistor" is used herein to refer to an electrically resistive component that includes semiconductor material with resistance that varies in response to a thermal change. Thus, a thermistor may be used in a resistive thermal sensor. Resistive thermal sensors may be made, for example, from materials with a high temperature coefficient of resistivity. Examples of such materials include, but are not limited to, amorphous silicon, vanadium oxide ($VO_x$), niobium oxide, yttrium barium copper oxide, and mercury cadmium telluride. Resistive thermal sensors may also or alternatively include other materials having a high temperature coefficient of resistivity, such as, for example, platinum, nickel, copper, iron-nickel alloys, tungsten, iridium, oxides of nickel, manganese, iron, cobalt, copper, magnesium, and titanium, and other metals, metal alloys, and oxides of metal.

The temperature sensors 105 may comprise, for example, thermocouples, which are electrical devices having two dissimilar electrical conductors forming electrical junctions at differing temperatures. As is known in the art, a thermocouple produces a temperature-dependent voltage caused by the thermoelectric effect. The produced voltage is a proxy for the measured temperature.

The temperature sensors 105 may comprise, for example, thermopiles. A thermopile comprises a plurality of thermocouples, which may be connected in series or in parallel, and converts thermal energy into electrical energy. A thermopile produces a voltage when its thermocouples are exposed to a temperature difference.

Figure 10:
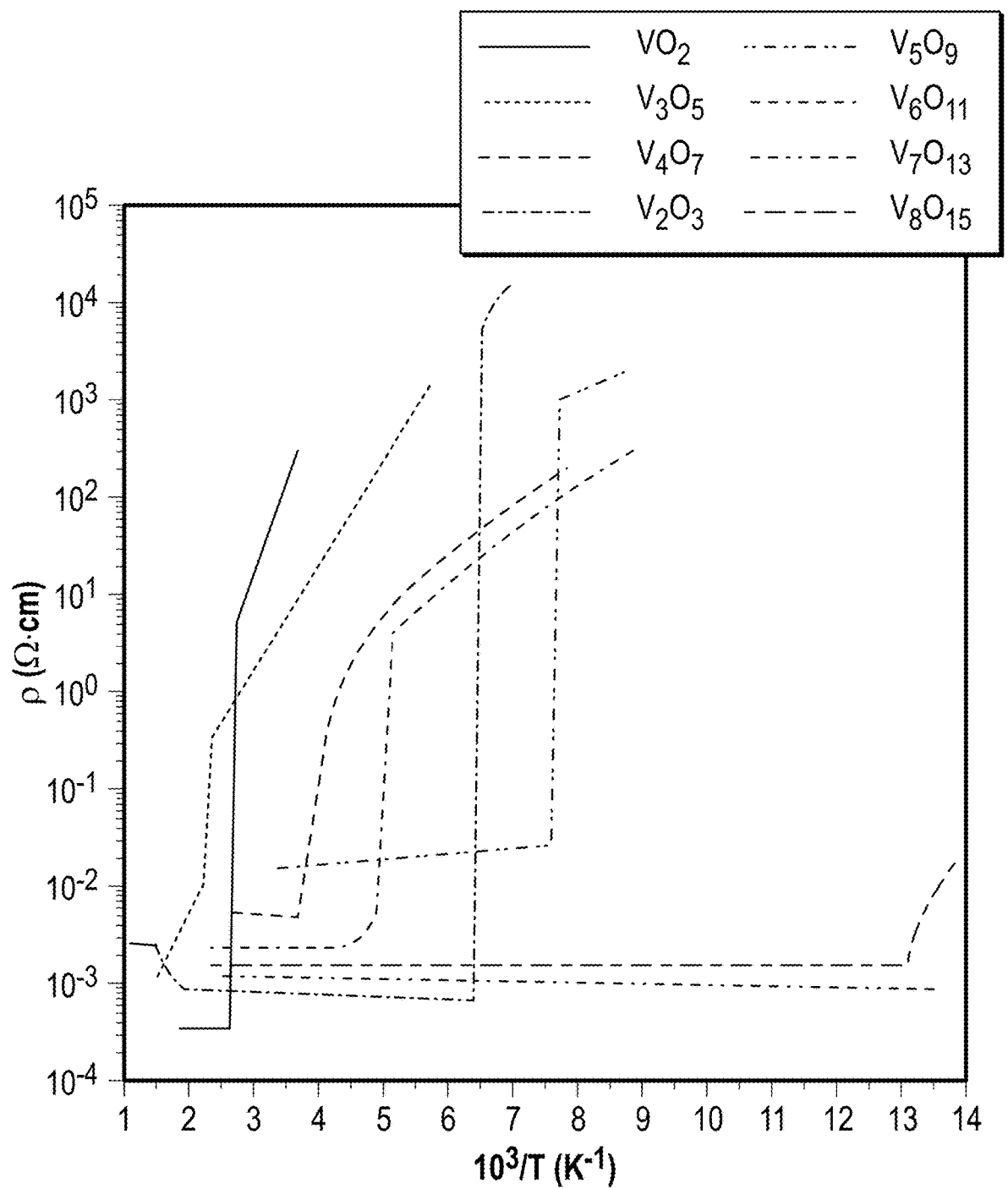
FIG. 10 illustrates the resistivity of various vanadium oxides as a function of the inverse of temperature, suitable for use in some embodiments.
Figure 11:
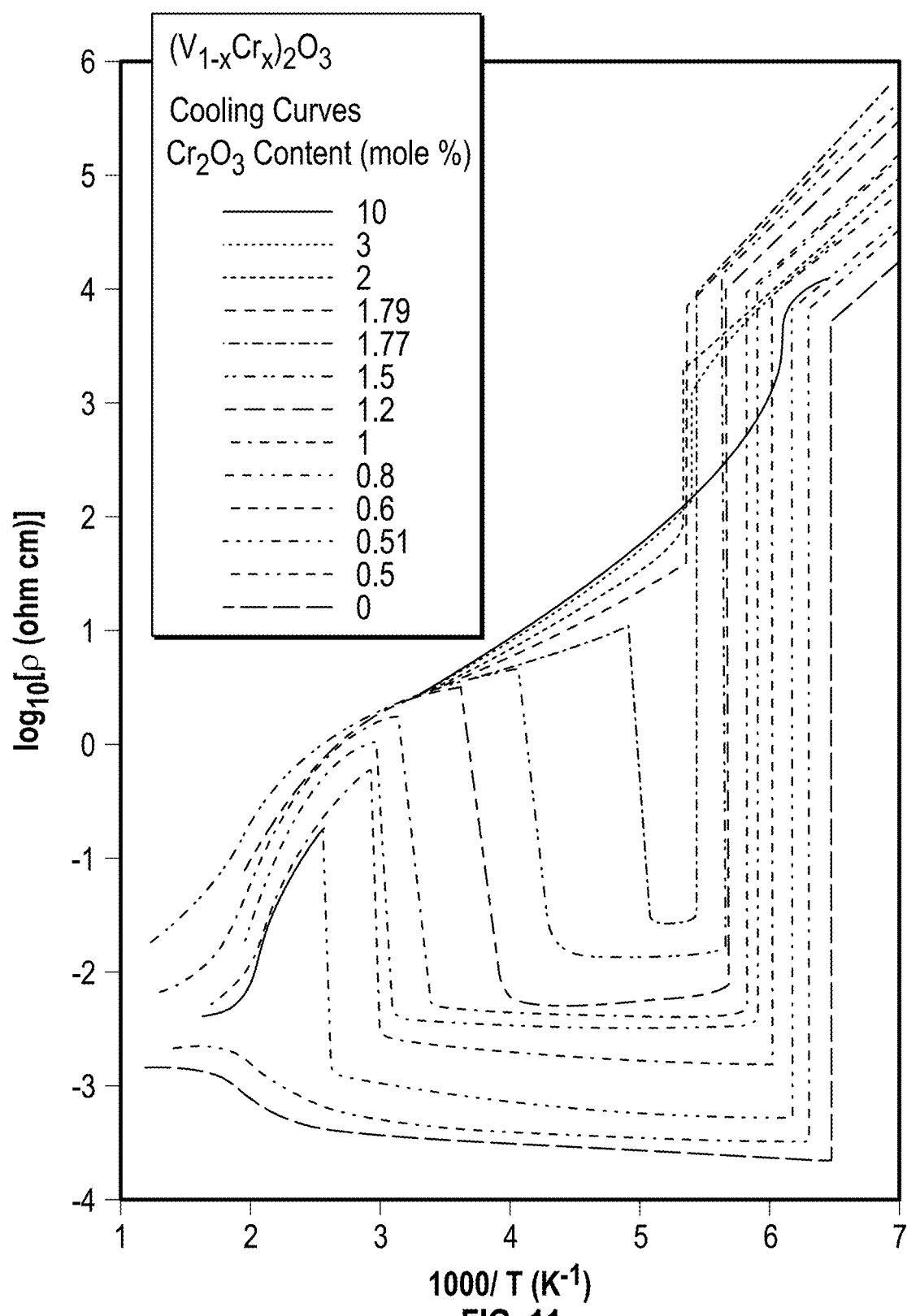
FIG. 11 illustrates that the transition temperature of vanadium oxide may be adjusted by doping, which may be suitable for use in some embodiments.

In some embodiments, the temperature sensors 105 comprise materials that provide a relatively large change in resistance for a small temperature change (e.g., 5% per degree Celsius over a wide range of temperatures and 200% per degree Celsius at the transition temperature). For example, in some embodiments, the temperature sensors 105 comprise vanadium oxide. Vanadium oxide has properties beneficial for use in the temperature sensors 105, including a relatively high temperature coefficient of resistance and low resistivity, as well as low electrical 1/f noise. FIG. 10 illustrates the resistivity of various vanadium oxides as a function of the inverse of temperature. As an example, as shown in FIG. 10, $VO_2$ has a transition temperature of 68 degrees Celsius, and there are many other vanadium oxides having different temperatures above and below 68 degrees Celsius that can be tuned over a wide range. The transition temperature may be adjusted by doping, as illustrated in FIG. 11. Suitable dopants that may be used in the temperature sensors include, for example, chromium and niobium.

In some embodiments, the temperature sensors 105 comprise amorphous silicon (a-Si). In some embodiments, the temperature sensors 105 comprise amorphous silicon-germanium (a-SiGe).

Figure 12:
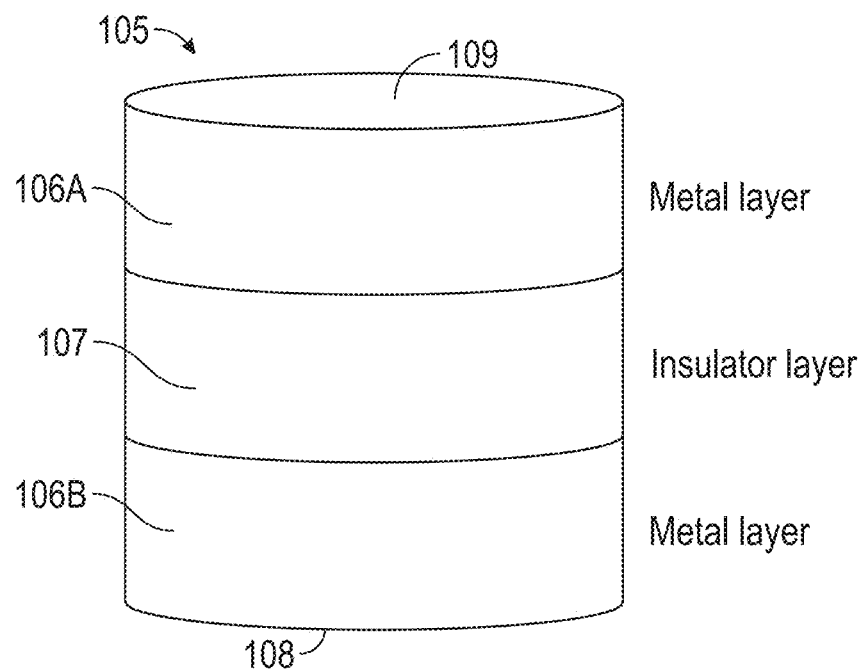
FIG. 12 illustrates an exemplary temperature sensor comprising a tunnel junction in accordance with some embodiments.

In some embodiments, the temperature sensors 105 comprise a tunnel junction that includes an insulator layer 107 between two conducting metal layers 106A and 106B, as shown in the exemplary temperature sensor of FIG. 12. The insulator layer 107 may be, for example, an oxide or nitride (e.g., aluminum oxide ($AlO_x$), magnesium oxide (MgO), tantalum oxide ($TaO_x$), titanium oxide ($TiO_x$), $HfO_2$, SiN, TaN, etc.). The metal layers 106A and 106B may comprise, for example, platinum, tantalum, tungsten, copper, titanium, etc.

Figure 13A:
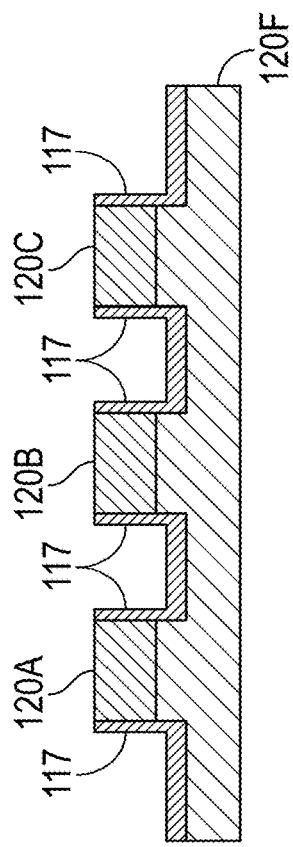
FIG. 13A shows an exemplary embodiment in which the temperature sensors are tunnel junctions in accordance with some embodiments.
Figure 13A:
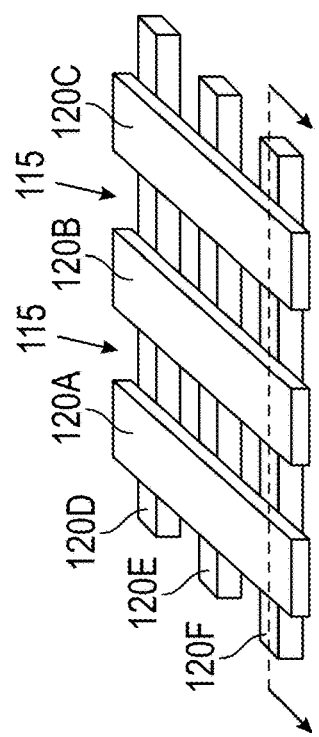

In some embodiments, the lines 120 themselves form a portion or all of the temperature sensors 105. For example, FIG. 13A shows an exemplary embodiment in which the temperature sensors 105 are tunnel junctions such as those shown and described in the context of FIG. 12, and the lines 120 themselves are the metal layers 106A and 106B. In the exemplary embodiment of FIG. 13A, the insulator layer 107 is deposited between the top lines 120A, 120B, and 120C and the bottom lines 120D, 120E, and 120F where they would otherwise intersect. For example, the metal layers 106A and 106B may comprise platinum, and the insulator layer 107 may comprise aluminum oxide. An insulating material may be deposited between the top lines 120 (e.g., between lines 120A and 120B and between lines 120B and 120C) to form the fluidic channel(s) 115 and to prevent MNPs in the fluidic channel(s) 115 from electrically shorting the temperature sensors 105. In some such embodiments, the resistance of the tunnel junction formed by the lines 120 and the insulator layer 107 changes in response to changes in the temperature. The embodiment of FIG. 13A may be used in conjunction with the selector elements 111 described in the context of FIGS. 9A and 9B above.

Figure 13B:
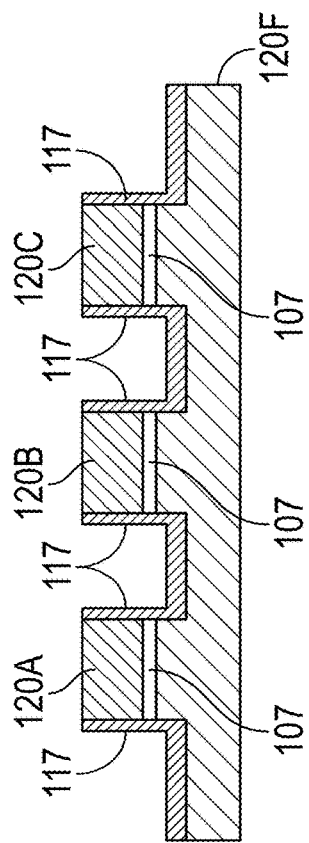
FIG. 13B is an example of a cross-point array architecture in which the temperature sensors are formed at the junctions of the top lines and the bottom lines in accordance with some embodiments.
Figure 13B:
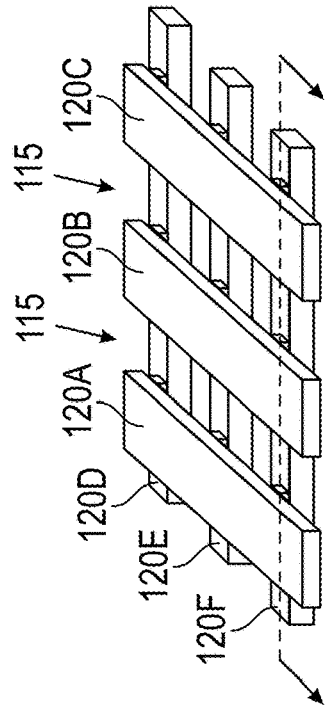

FIG. 13B is an example of a cross-point array architecture in which the temperature sensors 105 are formed at the junctions of the top lines 120A, 120B, 120C and the bottom lines 120D, 120E, 120F. The top lines 120 may comprise, for example, platinum (Pt), and the bottom lines 120 may comprise, for example, titanium (W), or vice versa. In such an architecture, the interfaces where the Pt and W overlap are the active regions in which the Seebeck effect produces a voltage signal. These interfaces are the regions of highest sensitivity to increases in temperature. Each temperature sensor 105 in such an architecture is a thermocouple formed at every location where a top line 120A, 120B, or 120C crosses a bottom line 120D, 120E, or 120F. An insulating material may be deposited between adjacent top lines 120 (e.g., between lines 120A and 120B and between lines 120B and 120C) to form the fluidic channel(s) 115 and to prevent MNPs in the fluidic channel(s) 115 from electrically shorting the temperature sensors 105. The embodiment of FIG. 13B may be used in conjunction with the selector elements described in the context of FIGS. 9A and 9B above. For example, CMOS select transistors may be used to address the individual thermocouple junctions to mitigate or prevent sneak currents and/or leakage current.

It is to be understood that the embodiments shown in FIGS. 12, 13A, and 13B are just a few examples of temperature sensors 105 that may be used in the various embodiments, and their discussion does not preclude the use of other types of temperature sensors 105, or other materials. Generally, the temperature sensors 105 may be any temperature sensors capable of detecting temperature changes caused by MNPs exposed to an alternating magnetic field. The exemplary configurations and materials described herein are not intended to be limiting.

Fabrication of Detection Device

Figure 14:
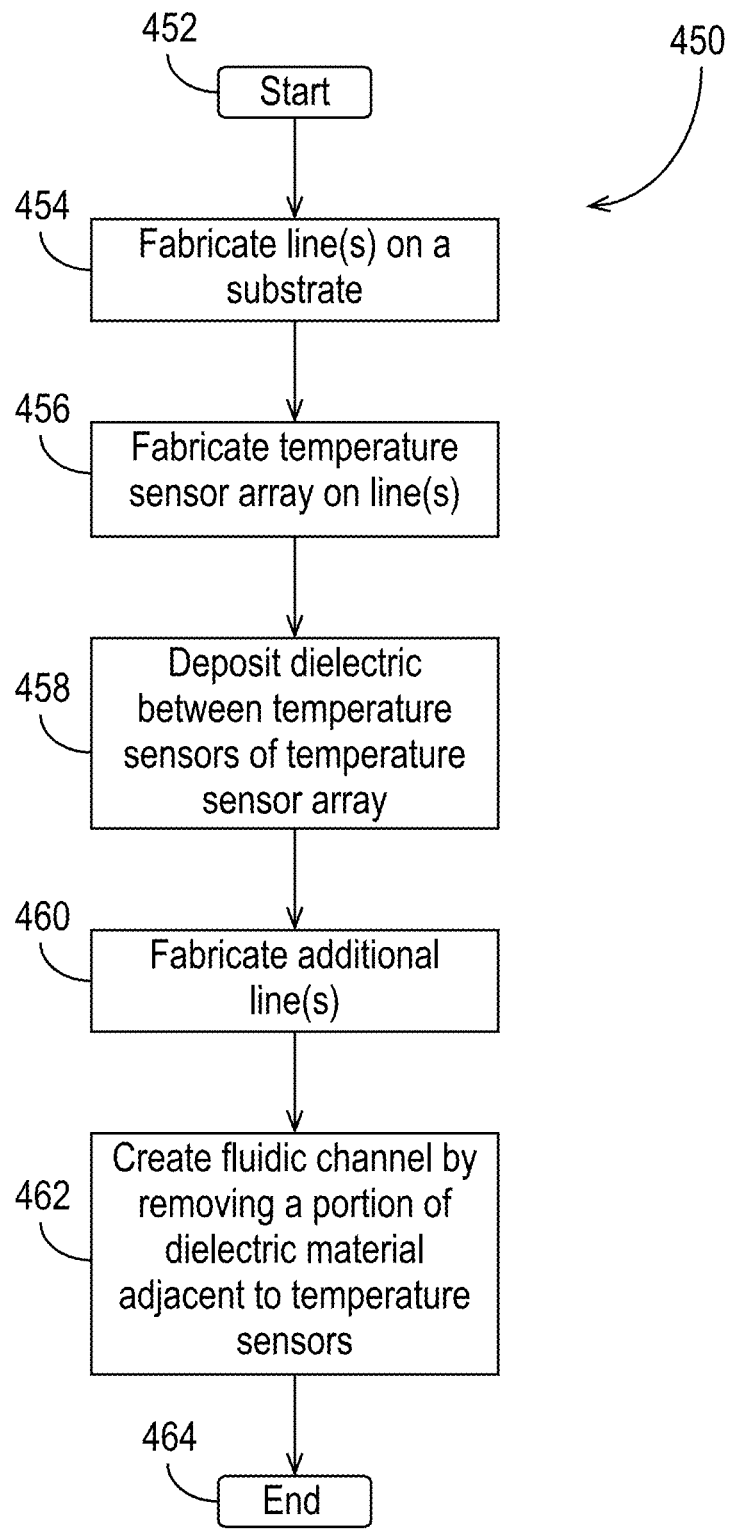
FIG. 14 illustrates a method of manufacturing the detection device in accordance with some embodiments.
Figure 15:
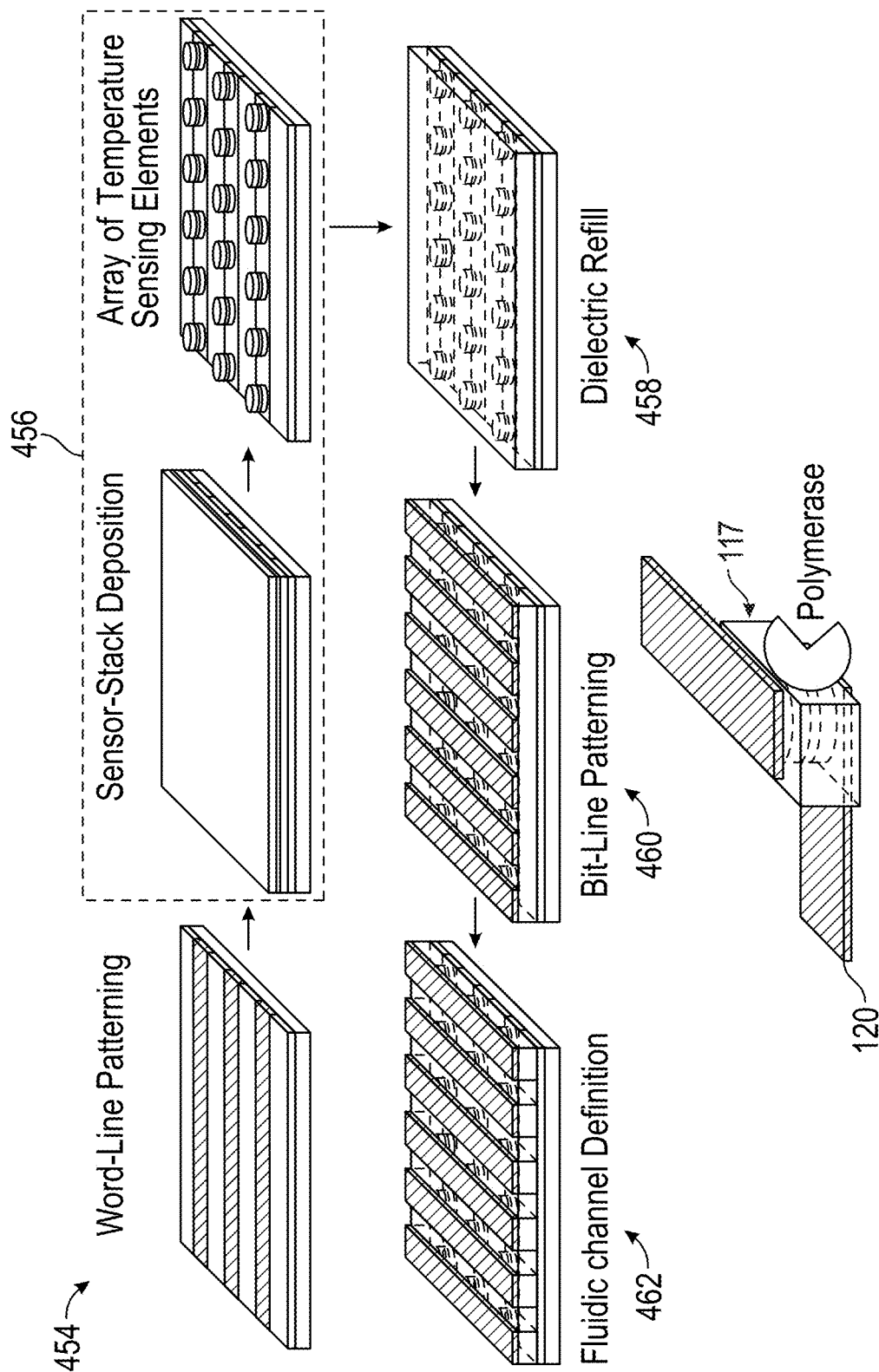
FIG. 15 illustrates the exemplary results of each step of the exemplary fabrication process illustrated in FIG. 14 in accordance with some embodiments.

In some embodiments, the detection device 100 is fabricated using photolithographic processes and thin film deposition. FIG. 14 illustrates an exemplary method 450 of manufacturing the detection device 100, and FIG. 15 illustrates the results of each step of the fabrication process 450 with a final panel showing polymerase bound to the wall 117 proximate to a temperature sensor 105 in accordance with some embodiments (e.g., when the detection device 100 is used for nucleic acid sequencing). At 452, the method begins. At 454, one or more lines 120 are fabricated on a substrate, for example, by depositing one or more metal layers, using, for example, photolithography to pattern an array of lines and spaces in a polymer layer applied on top of the metal layers, using that polymer layer as a mask for etching the metal layers into an array of lines, depositing an insulating dielectric material, stripping the polymer layer and dielectric material over the lines, and performing chemical mechanical polishing to planarize the surface. At 456, in some embodiments in which the lines 120 themselves do not form the temperature sensors 105, additional material (e.g., the insulator layer 107) forming at least a portion of the temperature sensor array 110 is fabricated on the one or more lines 120. In some such embodiments, each temperature sensor 105 of the temperature sensor array 110 has a bottom 108 and a top 109. (See FIG. 12.) The bottom 108 is coupled to (or indistinguishable from) at least one of the one or more lines 120. In some embodiments, the bottom 108 of each temperature sensor 105 is in contact with at least one of the one or more lines 120. In some embodiments, at least one of the one or more lines 120 forms part of at least one of the temperature sensors 105.

At 458, dielectric material is deposited between the temperature sensors 105 of the temperature sensor array 110. At 460, additional lines 120 are fabricated. Each of these additional lines 120 is coupled to (or forms) the top 109 of at least one temperature sensor 105 in the temperature sensor array 110. In some embodiments, the top 109 of each temperature sensor 105 is in contact with a line 120. In some embodiments, the bottom 108 of a temperature sensor 105 is in contact with a first line 120A, and the top 109 of the temperature sensor 105 is in contact with a second line 120B. In some embodiments, the first line 120A and the second line 120B form part or all of the temperature sensor 105. At 462, a portion of the dielectric material adjacent to the temperature sensors 105 is removed (e.g., by milling, etching, or any other suitable removal process) to create the fluidic channel(s) 115. At 464, the process 450 ends.

Although FIGS. 14 and 15 illustrate and describe exemplary steps in the fabrication process 450, it is to be understood that the fabrication process 450 may include any suitable techniques for depositing materials, such as, for example, growth of epitaxial material, physical vapor deposition (PVD), chemical vapor deposition (CVD), evaporation techniques, plating techniques, and/or spin coating. Similarly, the fabrication process 450 may include any suitable techniques for patterning materials, such as, for example, etching or otherwise removing exposed regions of thin films through a photolithographically-patterned resist layer or other patterned layer. Moreover, the fabrication process 450 may include techniques for polishing, planarizing, or otherwise modifying exposed surfaces of materials.

In embodiments in which the temperature sensors 105 comprise vanadium oxide, it may be desirable to fabricate the temperature sensors 105 at a higher temperature to improve the sensitivity of the temperature sensors 105. In some such embodiments, the fabrication process can include fabricating the temperature sensors 105 on a substrate made of p+ amorphous silicon so that the fabrication can incorporate higher-temperature fabrication for more sensitive thermal sensors, as well as enabling tighter tolerances that provide better balanced resistivity.

The embodiments described herein may have particular advantages that will be appreciated by those having skill in the art. For example, electrical detection methods for nucleic acid (e.g., DNA) sequencing have several advantages over conventional technologies involving optical detection methods. For example, methods involving electrical detection are not limited in terms of scaling flow cell dimensions in the same manner that optical detection is limited due to optical imaging being diffraction-limited.

In addition, in nucleic acid sequencing applications, electrical detection allows for simultaneous detection of all four bases using MNPs that, when exposed to an alternating magnetic field, cause distinguishable changes in the local temperature. Thus, a single base in the target DNA strand can be read using only one chemistry step. Because individual chemistry steps can take times on the order of minutes, the approaches disclosed herein can significantly speed up sequencing without reducing the read error rates.

To avoid obscuring the present disclosure unnecessarily, well-known components are shown in block diagram form and/or are not discussed in detail or, in some cases, at all. The drawings are not necessarily to scale, and the dimensions, shapes, and sizes of the features may differ substantially from how they are depicted in the drawings.

In the foregoing description and in the accompanying drawings, specific terminology has been set forth to provide a thorough understanding of the disclosed embodiments. In some instances, the terminology or drawings may imply specific details that are not required to practice the invention.

Unless otherwise specifically defined herein, all terms are to be given their broadest possible interpretation, including meanings implied from the specification and drawings and meanings understood by those skilled in the art and/or as defined in dictionaries, treatises, etc. As set forth explicitly herein, some terms may not comport with their ordinary or customary meanings.

The terms "over," "under," "between," "on", and other similar terms as used herein refer to a relative position of one layer with respect to other layers. As such, for example, one layer disposed over or under another layer may be directly in contact with the other layer or may have one or more intervening layers. Moreover, one layer disposed between layers may be directly in contact with the two layers or may have one or more intervening layers. In contrast, a first layer "on" a second layer is in contact with the second layer. The relative position of the terms does not define or limit the layers to a vector space orientation of the layers.

The terms "first," "second," etc. are used to distinguish between multiple instances of an item (e.g., a line, a temperature sensor, etc.). Unless the context indicates otherwise, the terms "first," "second," etc. are not used to convey a particular ordering of items. Likewise, the words "top" and "bottom" are used to distinguish between multiple instances of an item (e.g., lines). It is to be appreciated that in some contexts, "top" and "bottom" are interchangeable.

Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without other input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. The terms "exemplary" and "embodiment" are used to express examples, not preferences or requirements.

Disjunctive language such as the phrase "at least one of X, Y, Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present. As used in the specification and the appended claims, phrases of the form "at least one of A, B, and C," "at least one of A, B, or C," "one or more of A, B, or C," and "one or more of A, B, and C" are interchangeable, and each encompasses all of the following meanings: "A only," "B only," "C only," "A and B but not C," "A and C but not B," "B and C but not A," and "all of A, B, and C."

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

While the above detailed description has shown, described, and pointed out novel features as applied to various embodiments, it can be understood that various omissions, substitutions, and changes in the form and details of the devices or algorithms illustrated can be made without departing from the spirit of the disclosure. As can be recognized, certain embodiments described herein can be embodied within a form that does not provide all of the features and benefits set forth herein, as some features can be used or practiced separately from others.

We claim:

1. A method of using a detection device to detect presence and/or absence of magnetic nanoparticles, the detection device comprising at least one fluidic channel configured to receive a plurality of molecules to be detected, a plurality of temperature sensors, an insulating material encapsulating the plurality of temperature sensors and for providing a barrier between the plurality of temperature sensors and contents of the at least one fluidic channel, and detection circuitry coupled to the plurality of temperature sensors, the method comprising:
    subjecting the contents of the at least one fluidic channel to an alternating magnetic field;
    using the detection circuitry, and while subjecting the contents of the at least one fluidic channel to the alternating magnetic field, reading a temperature of a first temperature sensor of the plurality of temperature sensors, or detecting a change in temperature in a vicinity of the first temperature sensor; and
    determining, based on the temperature of the first temperature sensor or the change in temperature in the vicinity of the first temperature sensor, whether the first temperature sensor detected a magnetic nanoparticle (MNP).

2. The method of claim 1, wherein:
    reading the temperature of the first temperature sensor comprises detecting one or more of a resistance, current, or voltage across the first temperature sensor, and
    detecting the change in temperature in the vicinity of the first temperature sensor comprises detecting a change in the resistance, current, or voltage across the first temperature sensor.

3. The method of claim 1, wherein determining, based on the temperature of the first temperature sensor or the change in temperature in the vicinity of the first temperature sensor, whether the first temperature sensor detected the MNP comprises determining whether the temperature of the first temperature sensor or the change in temperature in the vicinity of the first temperature sensor is within a first range.

4. The method of claim 3, further comprising:
    recording whether the first temperature sensor detected the MNP.

5. The method of claim 3, wherein the first range is associated with a first MNP type, and wherein determining, based on the temperature of the first temperature sensor or the change in temperature in the vicinity of the first temperature sensor, whether the first temperature sensor detected the MNP further comprises determining whether the temperature of the first temperature sensor or the change in temperature in the vicinity of the first temperature sensor is within a second range, wherein the second range is associated with a second MNP type, and wherein the first range and the second range are non-overlapping.

6. The method of claim 5, further comprising:
    recording an identity of the MNP, wherein the identity identifies either the first MNP type or the second MNP type.

7. A method of detecting molecules using a detection device comprising a plurality of temperature sensors and a fluidic channel having a surface for binding molecules for detection by the plurality of temperature sensors, the method comprising:
    adding a first plurality of labeled molecules to the fluidic channel of the detection device, wherein each of the first plurality of labeled molecules is coupled to a first type of magnetic nanoparticle (MNP);
    applying an alternating magnetic field to the detection device;
    after adding the first plurality of labeled molecules to the fluidic channel of the detection device, and while applying the alternating magnetic field to the detection device, obtaining a temperature or temperature change at at least one temperature sensor of the plurality of temperature sensors; and for the at least one temperature sensor of the plurality of temperature sensors, detecting, based on the obtained temperature or temperature change, presence or absence of the first type of MNP.

8. The method of claim 7, further comprising:
in response to detecting the presence of the first type of MNP, recording, in a record, an identity of at least one of the plurality of labeled molecules to be detected.

9. The method of claim 7, further comprising:
heating or cooling an environment of the plurality of temperature sensors such that each of the plurality of temperature sensors is at a substantially same temperature, the substantially same temperature selected to achieve a target temperature sensitivity of the plurality of temperature sensors, and wherein obtaining the temperature or temperature change at the at least one temperature sensor of the plurality of temperature sensors comprises performing a temperature measurement while each of the plurality of temperature sensors is at the substantially same temperature.

10. The method of claim 9, wherein heating or cooling the environment of the plurality of temperature sensors comprises one or more of:
heating or cooling a fluid containing the plurality of labeled molecules to be detected,
heating or cooling the detection device, or
heating or cooling an environment of the detection device.

11. The method of claim 9, wherein heating or cooling the environment of the plurality of temperature sensors comprises:
applying a voltage or current to each temperature sensor of the plurality of temperature sensors.

12. The method of claim 7, further comprising:
adding a second plurality of labeled molecules to the fluidic channel of the detection device, wherein each of the second plurality of labeled molecules is coupled to a second type of MNP; and for the at least one temperature sensor of the plurality of temperature sensors, detecting, based on the obtained temperature or temperature change, presence or absence of the second type of MNP, and wherein obtaining the temperature or temperature change at the at least one temperature sensor of the plurality of temperature sensors follows adding the second plurality of labeled molecules to the fluidic channel of the detection device.

13. The method of claim 12, wherein adding the first plurality of labeled molecules to the fluidic channel of the detection device is performed at substantially a same time as adding the second plurality of labeled molecules to the fluidic channel of the detection device.

14. The method of claim 13, further comprising:
heating or cooling an environment of the plurality of temperature sensors such that each of the plurality of temperature sensors is at a substantially same temperature, the substantially same temperature selected to achieve a target temperature sensitivity of the plurality of temperature sensors, and wherein obtaining the temperature or temperature change at the at least one temperature sensor of the plurality of temperature sensors comprises performing a temperature measurement while each of the plurality of temperature sensors is at the substantially same temperature.

15. The method of claim 14, wherein heating or cooling the environment of the plurality of temperature sensors comprises one or more of:
heating or cooling a fluid containing the plurality of labeled molecules to be detected,
heating or cooling the detection device, or
heating or cooling an environment of the detection device.

16. The method of claim 14, wherein heating or cooling the environment of the plurality of temperature sensors comprises:
applying a voltage or current to each temperature sensor of the plurality of temperature sensors.

17. The method of claim 12, further comprising:
adding a third plurality of labeled molecules to the fluidic channel of the detection device, wherein each of the third plurality of labeled molecules is coupled to a third type of MNP; and for the at least one temperature sensor of the plurality of temperature sensors, detecting, based on the obtained temperature or temperature change, presence or absence of the third type of MNP, and wherein obtaining the temperature or temperature change at the at least one temperature sensor of the plurality of temperature sensors follows adding the third plurality of labeled molecules to the fluidic channel of the detection device.

18. The method of claim 17, wherein adding the first plurality of labeled molecules to the fluidic channel of the detection device, adding the second plurality of labeled molecules to the fluidic channel of the detection device, and adding the third plurality of labeled molecules to the fluidic channel of the detection device are performed at a substantially same time.

19. A method of using a detection system, the detection system comprising (a) at least one fluidic channel with a plurality of sites for binding a plurality of molecules to be detected, (b) a plurality of temperature sensors configured to detect, in presence of an alternating magnetic field, a temperature or temperature change indicating presence or absence of one or more magnetic nanoparticles (MNPs) coupled to at least one of the plurality of molecules to be detected at a respective subset of the plurality of sites, and (c) one or more magnetic components, the method comprising:
the one or more magnetic components subjecting a contents of the at least one fluidic channel to the alternating magnetic field;

while the one or more magnetic components are subjecting the contents of the at least one fluidic channel to the alternating magnetic field, detecting the temperature or temperature change at each of the plurality of temperature sensors; and based on the detected temperature or temperature change at a first temperature sensor of the plurality of temperature sensors, determining whether at least one MNP has been detected by a first temperature sensor of the plurality of temperature sensors.

20. The method of claim 19, wherein:
detecting the temperature or temperature change at each of the plurality of temperature sensors comprises detecting one or more of a resistance, current, or voltage across each of the plurality of temperature sensors or detecting a change in the resistance, current, or voltage across each of the plurality of temperature sensors.

21. The method of claim 19, wherein determining, based on the detected temperature or temperature change at a first temperature sensor of the plurality of temperature sensors, whether at least one MNP has been detected by the first temperature sensor comprises determining whether the detected temperature or temperature change at the first temperature sensor is within a first range.

22. The method of claim 21, further comprising:
recording whether the first temperature sensor detected the MNP.

23. The method of claim 21, wherein the first range is associated with a first MNP type, and wherein determining, based on the detected temperature or temperature change at the first temperature sensor, whether the first temperature sensor detected the MNP further comprises determining whether the detected temperature or temperature change at the first temperature sensor is within a second range, wherein the second range is associated with a second MNP type, and wherein the first range and the second range are non-overlapping.

24. The method of claim 23, further comprising:
recording an identity of the MNP, wherein the identity identifies either the first MNP type or the second MNP type.

* * * * *